(12) United States Patent
Terliuc et al.

(10) Patent No.: US 8,109,903 B2
(45) Date of Patent: Feb. 7, 2012

(54) CATHETER INCLUDING A BENDABLE PORTION

(75) Inventors: Gad Terliuc, Ra'anana (IL); Gilad Luria, Givataiim (IL); Ohad Shafran, Moshav Ein Ayala (IL)

(73) Assignee: SMART Medical Systems Ltd., Raanana (IL)

(*) Notice: Subject to any disclaimer, the term of this patent is extended or adjusted under 35 U.S.C. 154(b) by 0 days.

(21) Appl. No.: 12/600,838

(22) PCT Filed: May 20, 2008

(86) PCT No.: PCT/IL2008/000687
§ 371 (c)(1),
(2), (4) Date: May 11, 2008

(87) PCT Pub. No.: WO2008/142685
PCT Pub. Date: Nov. 27, 2008

(65) Prior Publication Data
US 2010/0217185 A1    Aug. 26, 2010

Related U.S. Application Data

(60) Provisional application No. 60/924,578, filed on May 21, 2007, provisional application No. 61/064,707, filed on Mar. 21, 2008, provisional application No. 61/064,735, filed on Mar. 24, 2008.

(51) Int. Cl.
*A61M 29/00* (2006.01)
(52) U.S. Cl. .................................................. 604/96.01
(58) Field of Classification Search ................ 604/96.01
See application file for complete search history.

(56) References Cited

U.S. PATENT DOCUMENTS

| 4,040,413 A | 8/1977 | Ohshiro |
| 4,066,070 A | 1/1978 | Utsugi |
| 4,148,307 A | 4/1979 | Utsugi |
| 4,176,662 A | 12/1979 | Frazer |
| 4,195,633 A | 4/1980 | Nehring et al. |
| 4,195,637 A | 4/1980 | Gruntzig et al. |

(Continued)

FOREIGN PATENT DOCUMENTS
WO    WO 83/01893    6/1983
(Continued)

OTHER PUBLICATIONS

An Office Action dated Sep. 28, 2009, which issued during the prosecution of Applicant's Australian Patent Application No. 2005211257.

(Continued)

*Primary Examiner* — Jackie Ho
*Assistant Examiner* — Diva Ranade
(74) *Attorney, Agent, or Firm* — Daniel J. Swirsky; AlphaPatent Associates Ltd.

(57) ABSTRACT

A catheter including a tube having at least one lumen, at least one elongate element, the at least one elongate element having a bendable portion at a predetermined bendable portion location therealong forward of a distal end of the tube and at least one selectably inflatable balloon communicating with at least one of the at least one lumen, the at least one selectably inflatable balloon having a forward end and a rearward end, the rearward end of the balloon being located rearwardly of the predetermined bendable portion location.

4 Claims, 32 Drawing Sheets

U.S. PATENT DOCUMENTS

| | | |
|---|---|---|
| 4,224,929 A | 9/1980 | Furihata |
| 4,445,892 A | 5/1984 | Hussein et al. |
| 4,453,545 A | 6/1984 | Inoue |
| 4,616,652 A | 10/1986 | Simpson |
| 4,646,722 A | 3/1987 | Silverstein et al. |
| 4,646,988 A | 3/1987 | Campbell |
| 4,676,228 A | 6/1987 | Krasner et al. |
| 4,807,593 A | 2/1989 | Ito |
| 4,862,874 A | 9/1989 | Kellner |
| 4,983,165 A | 1/1991 | Loiterman |
| 5,025,778 A | 6/1991 | Silverstein et al. |
| 5,050,585 A | 9/1991 | Takahashi |
| 5,135,001 A | 8/1992 | Sinofsky et al. |
| 5,259,366 A | 11/1993 | Reydel et al. |
| 5,518,501 A | 5/1996 | Oneda et al. |
| 5,577,992 A | 11/1996 | Chiba et al. |
| 5,662,587 A | 9/1997 | Grundfest et al. |
| 5,679,110 A | 10/1997 | Hamazaki |
| 5,762,604 A | 6/1998 | Kieturakis |
| 5,876,329 A | 3/1999 | Harhen |
| 5,938,586 A | 8/1999 | Wilk et al. |
| 6,007,482 A | 12/1999 | Madni et al. |
| 6,161,049 A | 12/2000 | Rudie et al. |
| 6,162,171 A | 12/2000 | Ng et al. |
| 6,309,346 B1 | 10/2001 | Farhadi |
| 6,461,294 B1 | 10/2002 | Oneda et al. |
| 6,485,409 B1 | 11/2002 | Voloshin et al. |
| 6,585,639 B1 | 7/2003 | Kotmel et al. |
| 6,663,589 B1 | 12/2003 | Halevy |
| 6,702,735 B2 | 3/2004 | Kelly |
| 6,951,554 B2 * | 10/2005 | Johansen et al. ............... 604/509 |
| 7,056,284 B2 | 6/2006 | Martone et al. |
| 7,169,105 B2 | 1/2007 | Iwasaka et al. |
| 7,780,715 B2 * | 8/2010 | Shaked et al. ............... 623/1.11 |
| 2002/0143237 A1 | 10/2002 | Oneda et al. |
| 2002/0156347 A1 | 10/2002 | Kim et al. |
| 2004/0102681 A1 | 5/2004 | Gross |
| 2005/0038335 A1 | 2/2005 | Gross et al. |
| 2005/0059931 A1 | 3/2005 | Garrison et al. |
| 2005/0124856 A1 | 6/2005 | Fujikura et al. |
| 2005/0125005 A1 | 6/2005 | Fujikura |
| 2005/0133453 A1 | 6/2005 | Woodruff et al. |
| 2005/0137457 A1 | 6/2005 | Machida |
| 2005/0159645 A1 | 7/2005 | Bertolero et al. |
| 2005/0165233 A1 | 7/2005 | Hamedi et al. |
| 2005/0165273 A1 | 7/2005 | Takano |
| 2005/0273021 A1 * | 12/2005 | Burgermeister ............... 600/585 |
| 2006/0111610 A1 | 5/2006 | Machida |
| 2006/0161044 A1 | 7/2006 | Oneda et al. |
| 2006/0241345 A1 | 10/2006 | Oishi et al. |
| 2007/0016165 A1 | 1/2007 | Von Oepen |
| 2007/0244361 A1 | 10/2007 | Ikeda et al. |

FOREIGN PATENT DOCUMENTS

| | | |
|---|---|---|
| WO | WO 99/53827 | 10/1999 |
| WO | WO 02/064028 | 8/2002 |
| WO | WO 03/080155 | 3/2003 |
| WO | WO 2004/101059 | 11/2004 |
| WO | WO 2004101059 A1 * | 11/2004 |

OTHER PUBLICATIONS

An Office Action dated Oct. 9, 2009, which issued during the prosecution of Applicant's U.S. Appl. No. 10/588,131.

An Office Action dated Apr. 9, 2010, which issued during the prosecution of Applicant's U.S. Appl. No. 10/588,131.

An Office Action dated Nov. 3, 2007, which issued during the prosecution of Applicant's Chinese Patent Application No. 200580004311.4.

An Office Action dated Jan. 25, 2010, which issued during the prosecution of Applicant's Chinese Patent Application No. 200810173921.2.

An International Search Report dated Sep. 1, 2005, which issued during the prosecution of Applicant's PCT/IL05/00152.

An International Search Report dated Jun. 2, 2010, which issued during the prosecution of Applicant's PCT/IL09/00940.

An International Search Report dated Sep. 1, 2009, which issued during the prosecution of Applicant's PCT/IL09/00322.

An International Search Report dated Jul. 9, 2009, which issued during the prosecution of Applicant's PCT/IL08/00687.

An International Search Report dated Jul. 18, 2008, which issued during the prosecution of Applicant's PCT/IL07/00832.

An International Search Report dated Apr. 21, 2008, which issued during the prosecution of Applicant's PCT/IL05/00849.

An International Search Report dated May 19, 2008, which issued during the prosecution of Applicant's PCT/IL07/00600.

Sleeve Expander Tool product, manufactured by HellermannTyton of 7930 N. Faulkner Road., Milwaukee, Wisconsin USA, and commercially distributed in the UK by Canford Audio PLC of Crowther Road, Washington, UK under catalog No. 55-601.

Double Balloon Endoscope product, including EN-450T5 enteroscope, TS-13140 overtube and BS-2 front balloon, which interface with balloon pump control BP-20 and 2200 video system, all commercially available from Fujinon Inc., of 10 High Point Drive, Wayne, New Jersey, USA.

Single Balloon Endoscope product, including SIF-Q 180 enteroscope, ST-SB1 overtube, which interface with balloon pump control OBCU and EVIS EXERA II system video system, all commercially available from Olympus Inc., of 3500 Corporate Parkway Center Valley, PA 18034-0610, USA.

An Office Action dated Mar. 23, 2009, which issued during the prosecution of Applicant's Israel Patent Application No. 177148. (Including a translation of the relevant part).

An English Abstract of JP 2003-250896, Sep. 2003.

An Office Action dated Sep. 23, 2009, which issued during the prosecution of Applicant's Israel Patent Application No. 177148. (Including a translation of the relevant part).

* cited by examiner

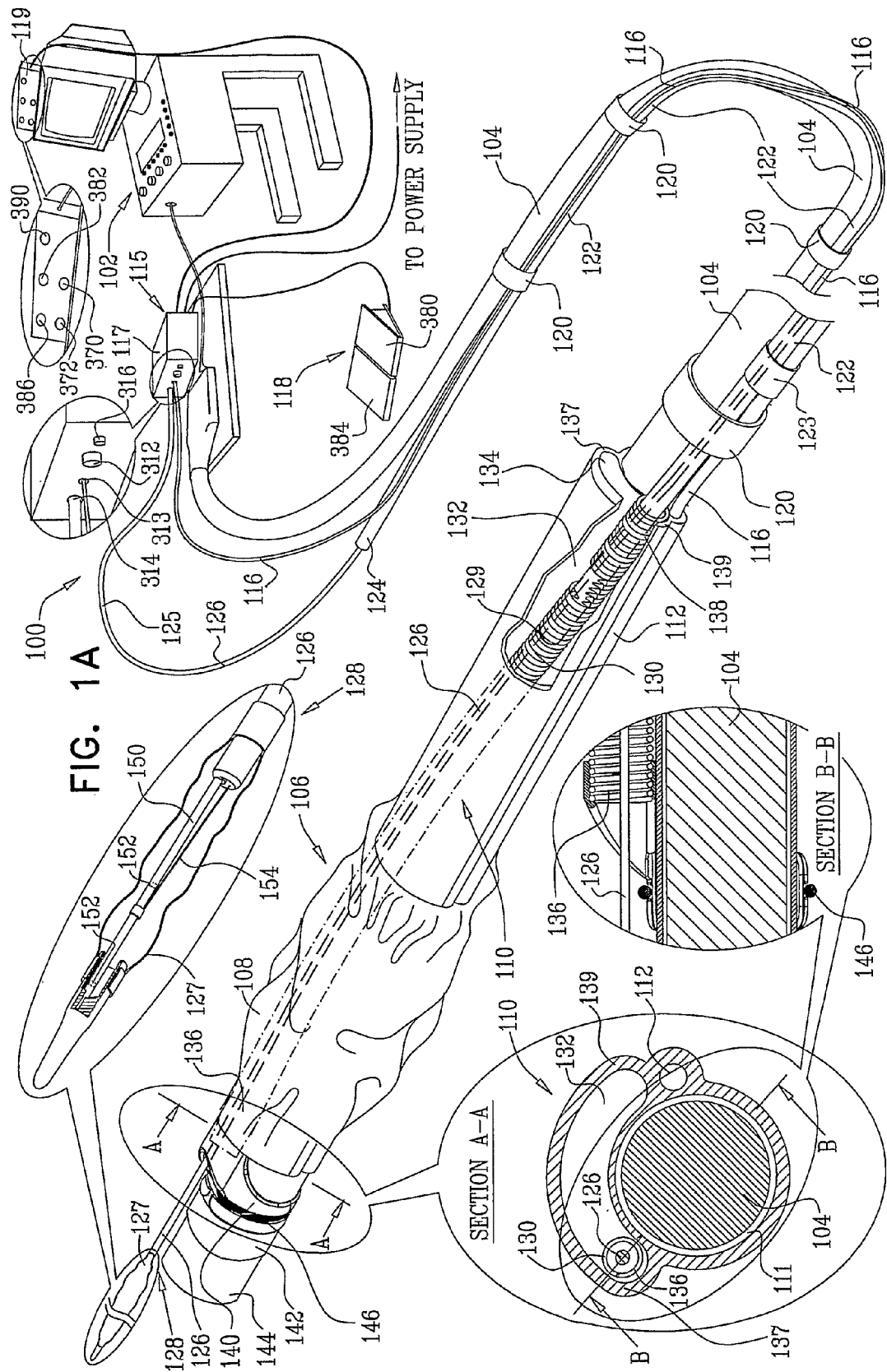

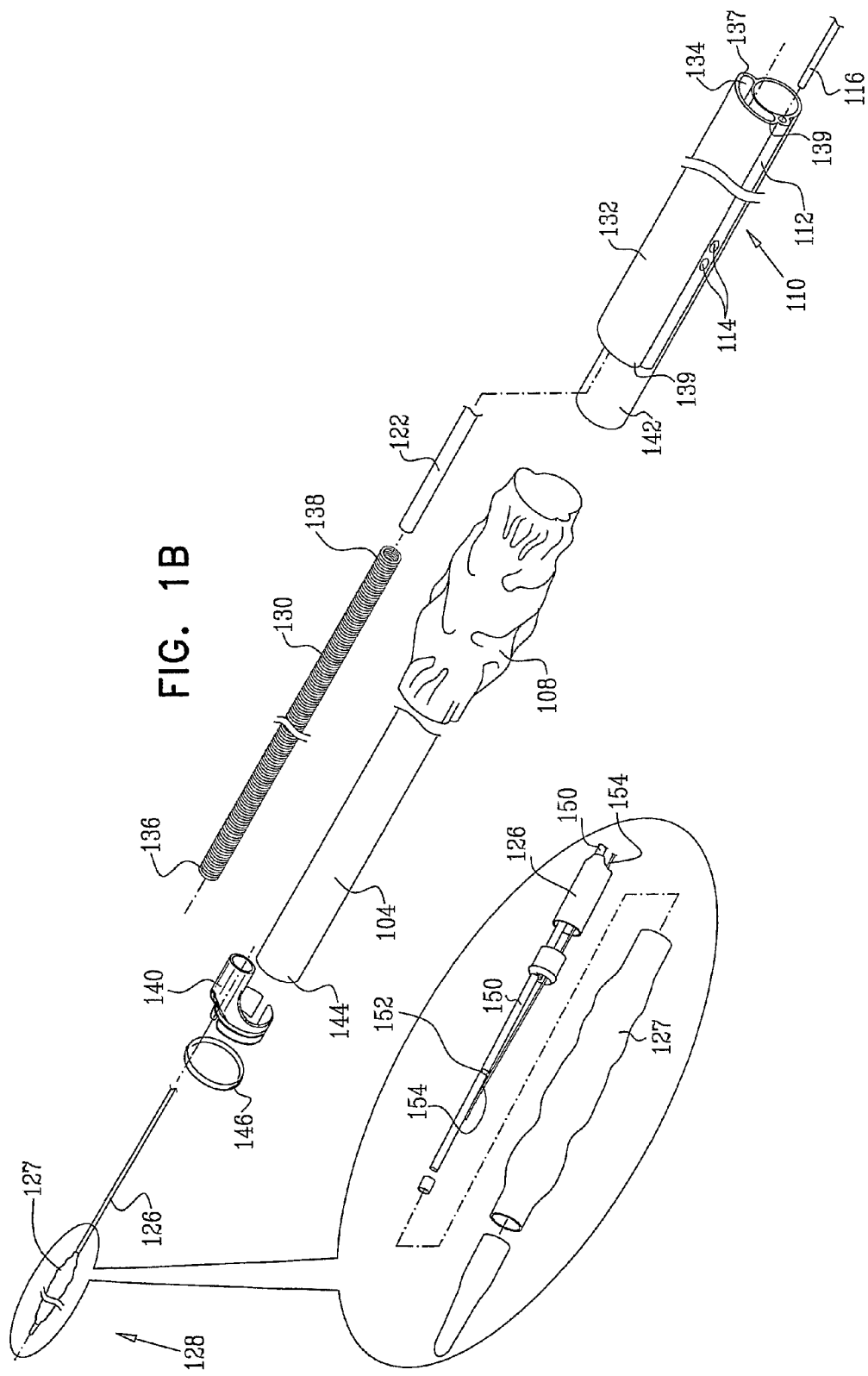

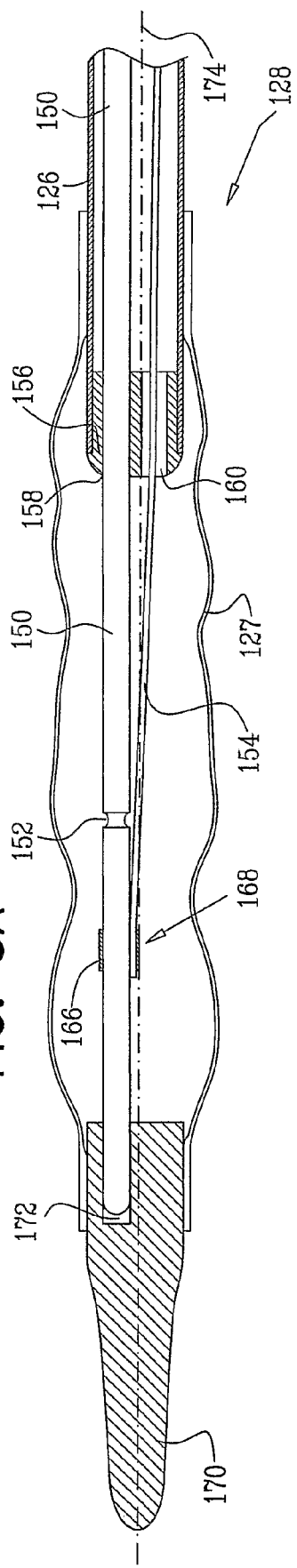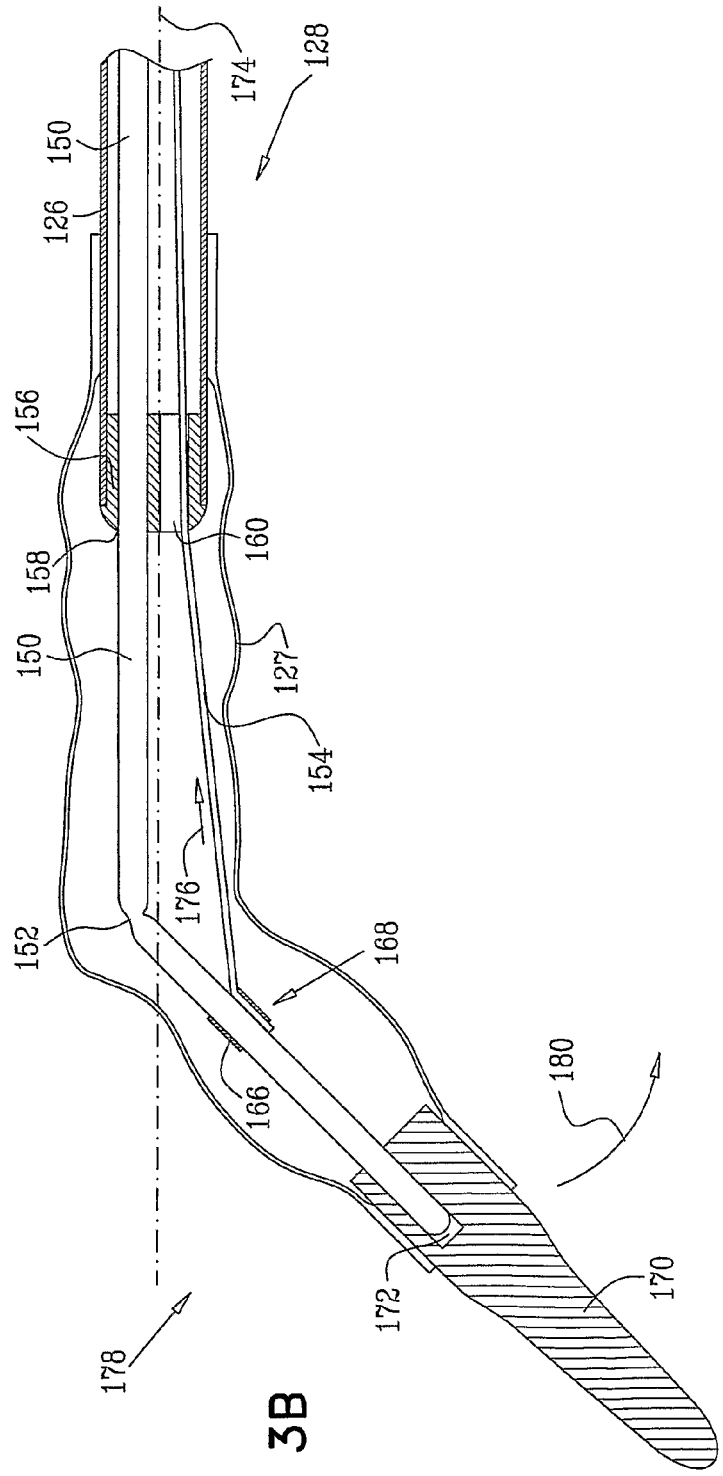
FIG. 3A
FIG. 3B

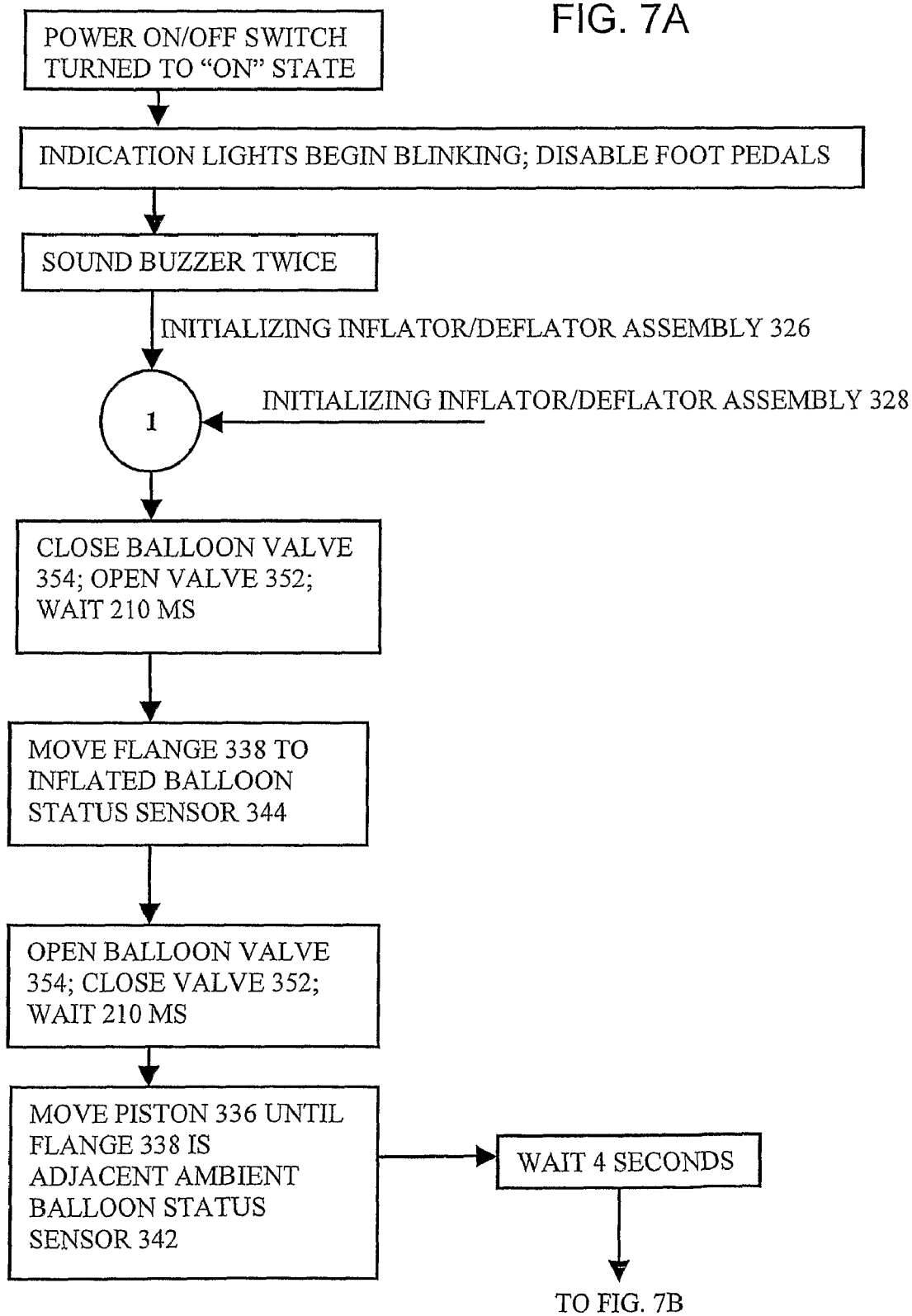

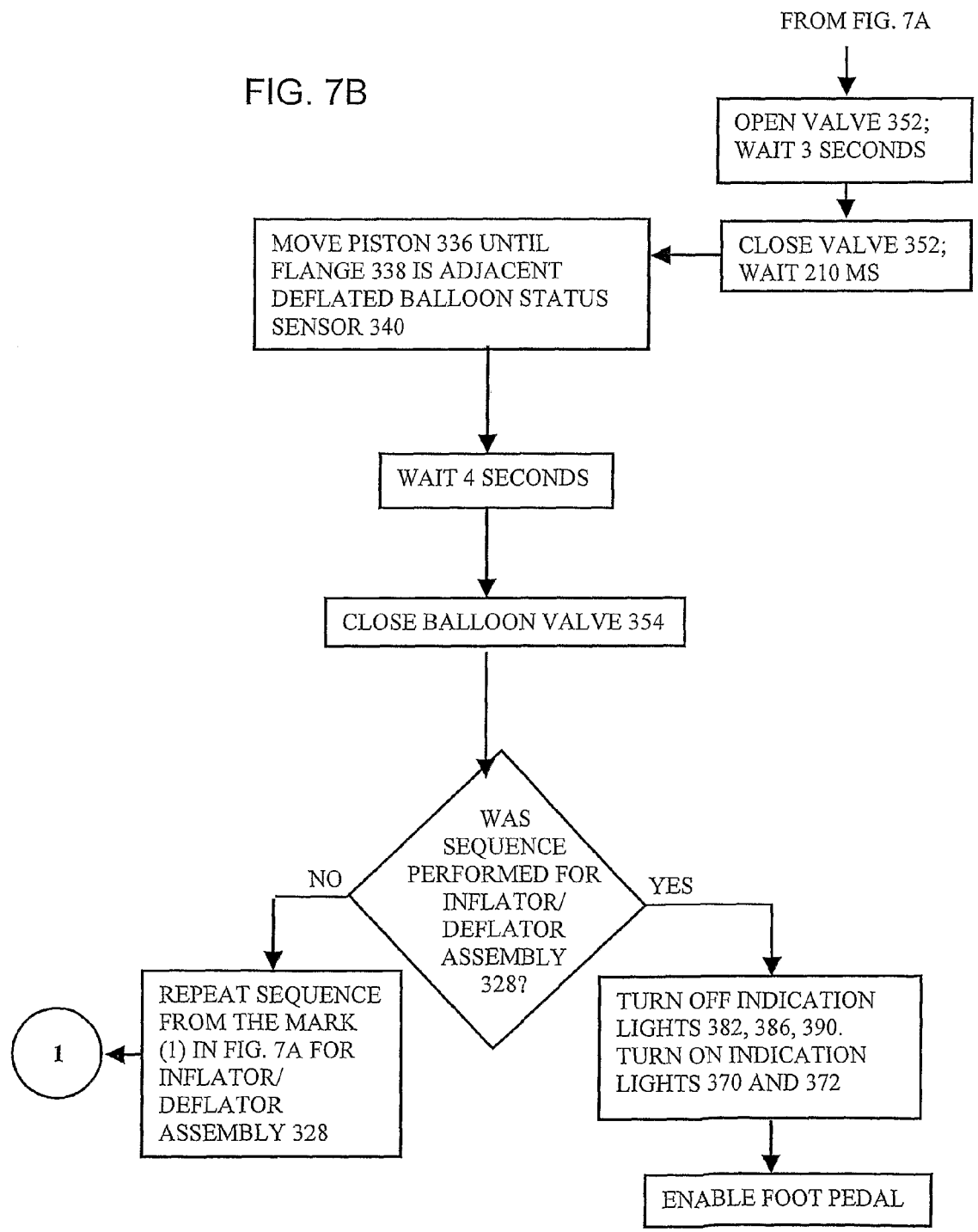

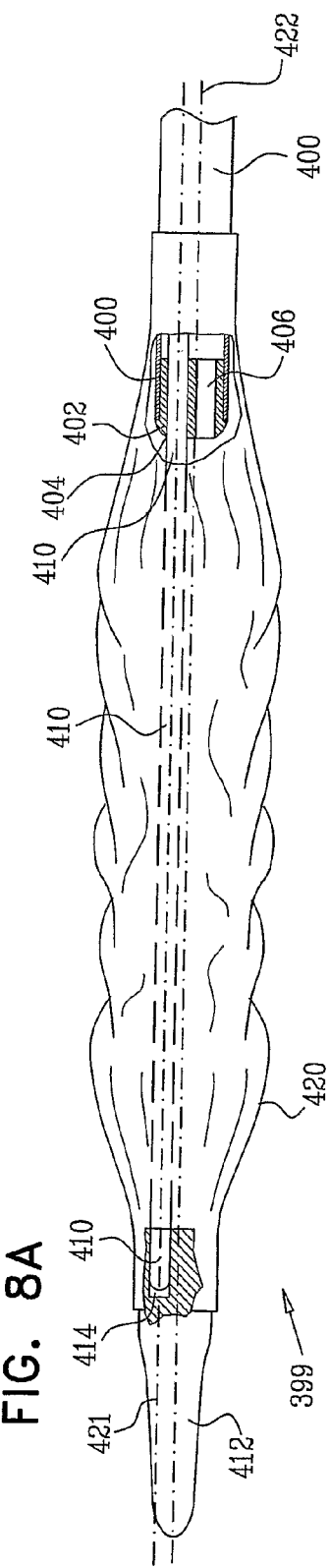
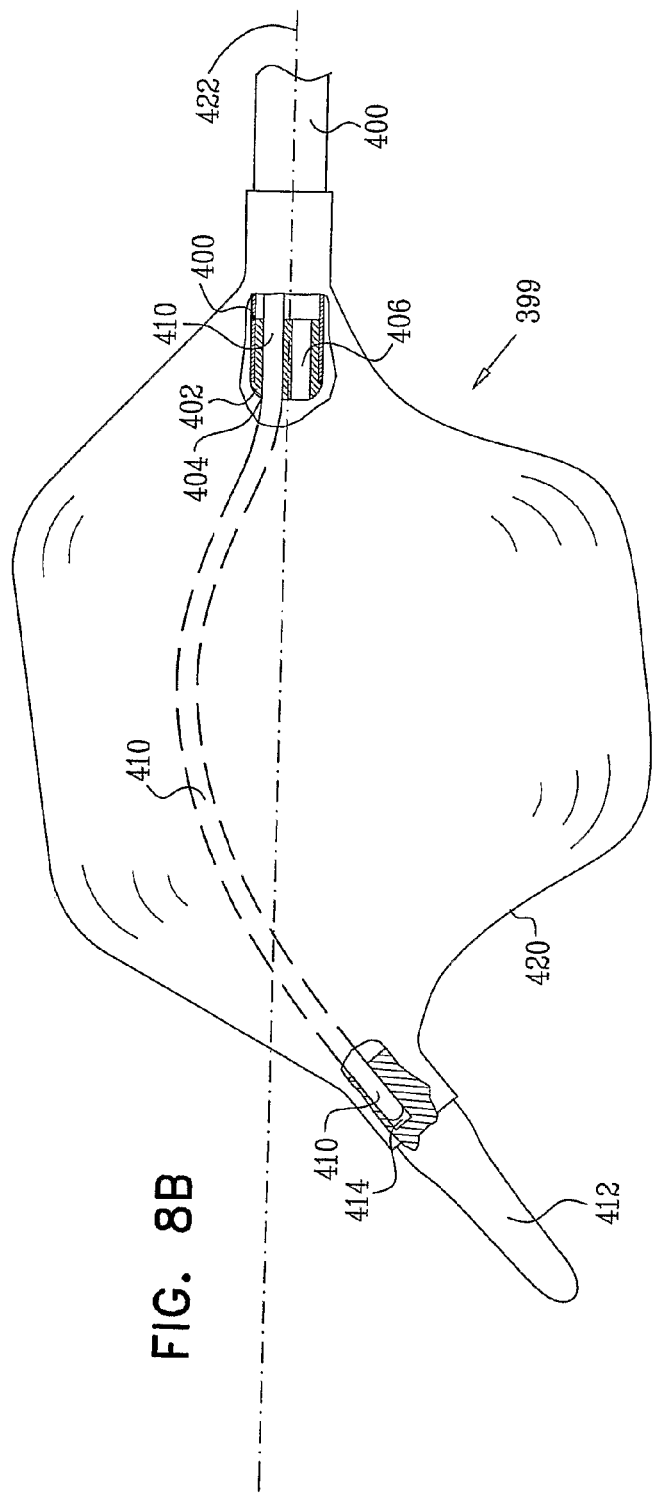

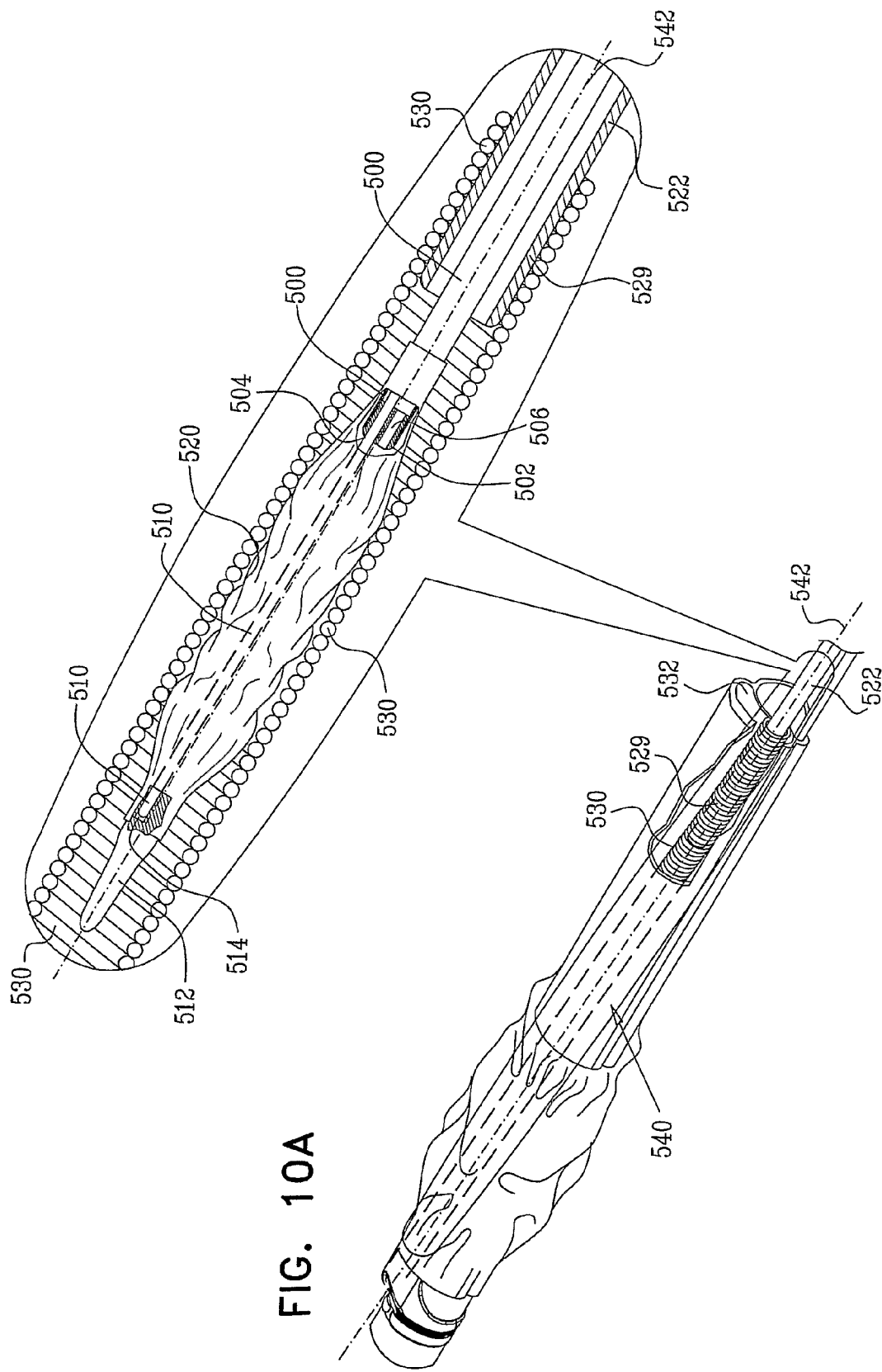

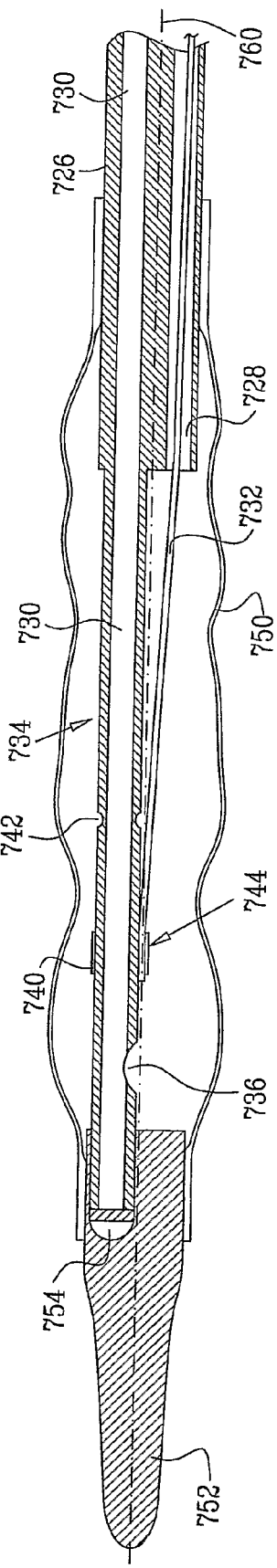

US 8,109,903 B2

CATHETER INCLUDING A BENDABLE PORTION

CROSS-REFERENCE TO RELATED APPLICATIONS

This application is a U.S. National Phase Application under 35 U.S.C. 371 of PCT International Application No. PCT/IL2008/000687, which has an international filing date of May 20, 2008. Reference is made to the following related applications, the disclosures of which are hereby incorporated by reference and priority of which is hereby claimed pursuant to 35 U.S.C. 37 CFR 1.78(a) (4) and (5)(i):

PCT Application No. PCT/IL2007/000600, filed May 17, 2007; U.S. Provisional Patent Application Ser. No. 60/924,578, filed May 21, 2007, entitled BALLOON CATHETER WITH UNIQUE GUIDEWIRE ASSEMBLY;

U.S. Provisional Patent Application Ser. No. 61/064,707, filed Mar. 21, 2008, entitled EXTERNAL CHANNEL FOR ELONGATED MEDICAL INSTRUMENTS; and U.S. Provisional Patent Application Ser. No. 61/064,735, filed Mar. 24, 2008, entitled BALLOON ASSEMBLY FOR ENDOSCOPY.

Reference is also made to applicant's copending PCT Application No. PCT/IL2005/000152, filed Feb. 7, 2005; and PCT Application No. PCT/IL2005/000849, filed Aug. 8, 2005, the disclosures of which are hereby incorporated by reference.

FIELD OF THE INVENTION

The present invention relates to catheters generally.

BACKGROUND OF THE INVENTION

The following patent publications are believed to represent the current state of the art:
U.S. Pat. Nos. 7,169,105 and 7,056,284.

SUMMARY OF THE INVENTION

The present invention seeks to provide an improved catheter. The term "catheter" is used to define a medical device including a hollow tube which may be passed into a body for investigation and/or treatment.

There is thus provided in accordance with a preferred embodiment of the present invention a catheter including a tube having at least one lumen, at least one elongate element, the at least one elongate element having a bendable portion at a predetermined bendable portion location therealong forward of a distal end of the tube and at least one selectably inflatable balloon communicating with at least one of the at least one lumen, the at least one selectably inflatable balloon having a forward end and a rearward end, the rearward end of the balloon being located rearwardly of the predetermined bendable portion location.

Preferably, the forward end of the balloon is located rearwardly of the predetermined bendable portion location. Alternatively, the forward end of the balloon is located forwardly of the predetermined bendable portion location.

In accordance with a preferred embodiment of the present invention the catheter also includes a steering element coupled to the elongate element forwardly of the predetermined bendable portion location. Additionally, the steering element is manipulatable by an operator for steering of the catheter. Additionally or alternatively, the steering element is operative to apply a pulling force to a distal portion of the elongate element.

Preferably, the pulling force causes the distal portion to rotate relative to a longitudinal axis of the catheter. Additionally, the at least one elongate element is resilient and returns to its axial orientation when the pulling force is no longer applied thereto.

In accordance with a preferred embodiment of the present invention a diameter of the balloon when fully inflated is in the range of 35-45 mm.

There is also provided in accordance with another preferred embodiment of the present invention a catheter including a tube having at least one lumen and having a bendable portion at a predetermined bendable portion location therealong and at least one selectably inflatable balloon communicating with at least one of the at least one lumen, the at least one selectably inflatable balloon having a forward end and a rearward end, the rearward end of the balloon being located rearwardly of the predetermined bendable portion location.

Preferably, the forward end of the balloon is located rearwardly of the predetermined bendable portion location. Alternatively, the forward end of the balloon is located forwardly of the predetermined bendable portion location.

In accordance with a preferred embodiment of the present invention the catheter also includes a steering element coupled to the tube forwardly of the predetermined bendable portion location. Additionally, the steering element is manipulatable by an operator for steering of the catheter. Additionally or alternatively, the steering element is operative to apply a pulling force to a distal portion of the tube.

Preferably, the pulling force causes the distal portion to rotate relative to a longitudinal axis of the catheter. Additionally, the tube is resilient and returns to its axial orientation when the pulling force is no longer applied thereto.

In accordance with a preferred embodiment of the present invention a diameter of the balloon when fully inflated is in the range of 35-45 mm.

There is further provided in accordance with yet another preferred embodiment of the present invention a catheter including a tube having at least one lumen, at least one elongate element, at least part of which is extendable forwardly of a distal end of the tube to a fixed orientation at which a distal end of the at least one elongate element extends beyond the distal end of the tube by a fixed amount and at least one selectably inflatable balloon communicating with at least one of the at least one lumen, the at least one selectably inflatable balloon having a forward end and a rearward end, the rearward end of the balloon being located adjacent the distal end of the tube at a rearward balloon end mounting location and the forward end of the balloon being located adjacent a distal end of the at least one elongate element at a forward balloon end mounting location, wherein the balloon is configured such that when the at least one elongate element is in the fixed orientation and the balloon is in a deflated operative orientation, the distance between the rearward balloon end mounting location and the forward balloon end mounting location is greater than the distance between the rearward balloon end mounting location and the forward balloon end mounting location when the balloon is an inflated operative orientation, thereby producing bowing of the at least one elongate element upon inflation of the balloon.

Preferably, the distance between the rearward balloon end mounting location and the forward balloon end mounting location is greater than the distance between the rearward balloon end mounting location and the forward balloon end mounting location when the balloon is an inflated operative orientation by at least 20%. Additionally or alternatively, the bowing of the elongate element is in a predetermined direction. Alternatively or additionally, the bowing of the elongate element produces an asymmetric, inflated balloon configuration.

There is even further provided in accordance with still another preferred embodiment of the present invention a catheter including a tube having at least one lumen and at least one selectably inflatable asymmetrical balloon communicating with at least one of the at least one lumen, the at least one selectably inflatable asymmetrical balloon having a forward end and a rearward end, the balloon, when not inflated, having a generally tapered forward facing portion having increasing diameter from the forward end toward the rearward end and a generally tapered rearward facing portion having decreasing diameter from the forward end toward the rearward end, the extent of tapering of the forward and rearward facing portions being different.

Preferably, the extent of tapering of the forward portion is less than the extent of tapering of the rearward portion.

There is also provided in accordance with another preferred embodiment of the present invention an endoscope system including an endoscope, an external tube associated with the endoscope and extending alongside the endoscope; an endoscope tool extending through the external tube and having formed along at least part of an elongate surface thereof a hydrophilic coating and a liquid communication port associated with the external tube for providing liquid communication with the interior of the external tube.

There is further provided in accordance with yet another preferred embodiment of the present invention for use with an endoscope, an external tube assembly including an external tube associated with the endoscope and extending alongside the endo scope, an endoscope tool extending through the external tube and having formed along at least part of an elongate surface thereof a hydrophilic coating and a liquid communication port associated with the external tube for providing liquid communication with the interior of the external tube.

There is even further provided in accordance with still another preferred embodiment of the present invention an endoscope system including an endoscope, an external tube associated with the endoscope and extending alongside the endoscope and a drainage vessel associated with the external tube for receiving liquid from the interior of the external tube.

There is also further provided in accordance with a further preferred embodiment of the present invention for use with an endoscope, an external tube assembly including an external tube associated with the endoscope and extending alongside the endoscope and a drainage vessel associated with the external tube for receiving liquid from the interior of the external tube.

There is further provided in accordance with another preferred embodiment of the present invention an enhanced flexibility auxiliary endoscope assembly for use with an endoscope, the assembly including at least one flexible elongate element, a flexible sleeve having a first lumen for accommodating a distal portion of an endoscope and a second lumen for accommodating the at least one flexible elongate element and an inflatable balloon mounted onto the flexible sleeve, the inflatable balloon, when in a non-inflated state, having a forwardly facing generally tapered end and a rearwardly facing generally tapered end, the forwardly facing generally tapered end having a slope which is less steep than a corresponding slope of the rearwardly facing generally tapered end.

BRIEF DESCRIPTION OF THE DRAWINGS

The present invention will be understood and appreciated more fully from the following detailed description, taken in conjunction with the drawings in which:

FIGS. 1A and 1B are, respectively, pictorial and exploded view simplified illustrations of a flexible endoscope system constructed and operative in accordance with a preferred embodiment of the present invention;

FIGS. 3A and 3B are sectional illustrations of the catheter or endoscope tool of FIGS. 2A & 2B in respective straight and bent operative steering orientations;

FIGS. 7A, 7B, 7C and 7D are simplified flow charts illustrating preferred modes of operation of the inflation control unit of FIGS. 6A-6C;

FIGS. 8A and 8B are simplified partially cut away illustrations of a balloon catheter constructed and operative in accordance with a preferred embodiment of the present invention;

FIGS. 10A and 10B are simplified, partially cut away, partially sectional, illustrations of a balloon catheter/external tube assembly constructed and operative in accordance with a preferred embodiment of the present invention;

FIGS. 16A and 16B are sectional illustrations of the catheter or endoscope tool of FIGS. 15A & 15B in respective straight and bent operative steering orientations.

DETAILED DESCRIPTION OF PREFERRED EMBODIMENTS

Figure 2A:
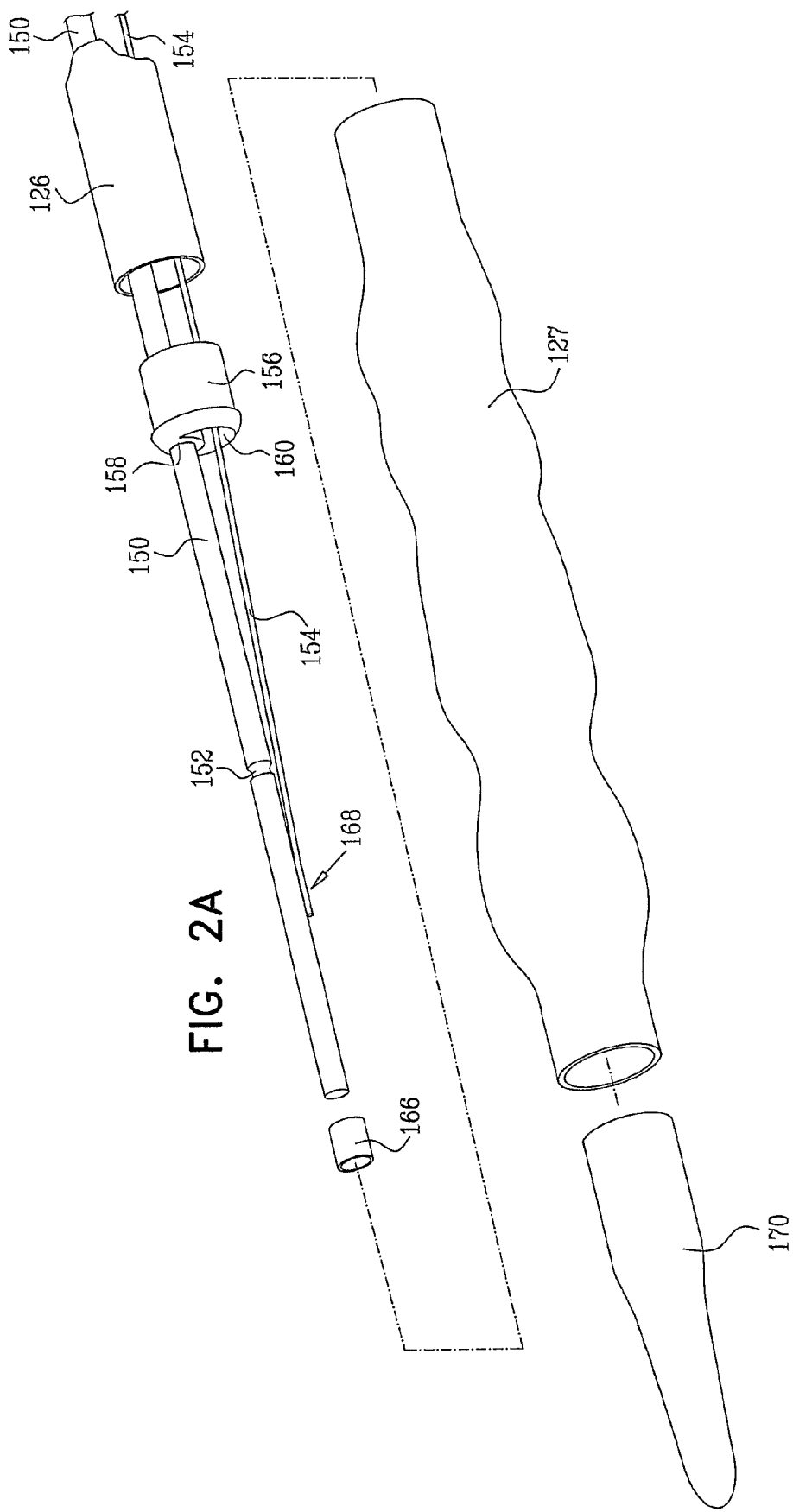
FIGS. 2A and 2B are respective exploded and partially cut-away pictorial illustrations of a catheter or endoscope tool and associated inflation tube, constructed and operative in accordance with a preferred embodiment of the present invention.

The terms "endoscope" and "endoscopy" are used throughout in a manner somewhat broader than their customary meaning and refer to apparatus and methods which operate within body cavities, passageways and the like, such as, for example, the small intestine, the large intestine, arteries and veins. Although these terms normally refer to visual inspection, as used herein they are not limited to applications which employ visual inspection and refer as well to apparatus, systems and methods which need not necessarily involve visual inspection.

The term "distal" refers to the remote end of an endoscope, accessory or tool furthest from the operator.

The term "proximal" refers to the end portion of an endoscope, accessory or tool closest to the operator, typically outside an organ or body portion of interest.

Reference is now made to FIGS. 1A & 1B, which illustrate an endoscopy system 100 constructed and operative in accordance with a preferred embodiment of the present invention. The endoscopy system 100 preferably includes a console 102, such as a console including a EPK-1000 video processor and a SONY LMD-2140MD medical grade flat panel LCD monitor, all commercially available from Pentx Europe GmbH, 104 Julius-Vosseler St., 22527 Hamburg, Germany. The system 100 preferably includes a conventional flexible endoscope 104, such as a VSB-3430K video enteroscope or a EC-3470LK video colonoscope which are commercially available from Pentx Europe GmbH, 104 Julius-Vosseler St., 22527 Hamburg, Germany.

In accordance with a preferred embodiment of the invention, an auxiliary endoscopy assembly 106 comprising a peripheral balloon 108 may be mounted onto endoscope 104 as shown, by means of a tubular sleeve 110 having a central lumen 111 which is placed over part of the distal portion of endoscope 104, and is associated with peripheral balloon 108. Many of the features of auxiliary endoscopy assembly 106 are described in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

It is appreciated that the tubular sleeve 110 may be constructed of a flexible and stretchable material, such as flexible and stretchable silicon, latex or rubber, thereby enabling it to conform with bending of endoscope 104. It is further appreciated that tubular sleeve 110 preferably has an untensioned inner circumference slightly larger than the cross-sectional circumference of endoscope 104, thereby allowing it to be pulled and slid over the endoscope 104.

As illustrated in FIGS. 1A & 1B, peripheral balloon 108 at least partially overlays tubular sleeve 110 at a location adjacent a distal end of tubular sleeve 110, and is fixed thereon at both edges by any suitable conventional means, such as an adhesive, in order to define a sealed volume therebetween. Preferably, inflation and deflation of peripheral balloon 108 is provided via a lumen 112, which preferably is defined by tubular sleeve 110 and communicates with the interior of peripheral balloon 108 via at least one aperture 114. Lumen 112 preferably communicates with an inflation control assembly 115 via a tube 116. Inflation control assembly 115 preferably comprises a control unit 117 having associated therewith dual foot pedals 118 and an operational status indicator panel 119.

Tube 116 may be attached to endoscope 104 at multiple locations along its length by any suitable conventional means such as medical adhesive tape or flexible bands 120.

It is appreciated that in accordance with a preferred embodiment of the present invention peripheral balloon 108 is generally inflatable, and can be inflated to a diameter about 3-10 times larger than its diameter when not inflated. In accordance with a preferred embodiment of the present invention, useful for small intestine endoscopy, the diameter of peripheral balloon 108 when fully inflated is in the range of 35-45 mm. Preferably, inflation of the peripheral balloon 108 to a diameter less than 45 mm may be achieved using relatively low pressure, such as in the range of 30-70 millibars.

In another specific embodiment, useful for large intestine endoscopy, the diameter of the peripheral balloon, when fully inflated, is in the range of 4-6 centimeters. In a further embodiment, also useful for large intestine endoscopy, the diameter of the peripheral balloon, when fully inflated, is six centimeters. Preferably, inflation of the peripheral balloon 108 to a diameter less than six centimeters may be achieved using relatively low pressure, such as in the range of 30-70 millibars.

It is appreciated that in accordance with a preferred embodiment of the present invention, useful for in vivo inspection of a generally tubular body portion having a variable cross-sectional diameter, the expansion diameter range of peripheral balloon 108 is larger than the maximum cross-sectional diameter of the generally tubular body portion, thereby enabling engagement of expanded peripheral balloon 108 with the interior surface of the generally tubular body portion, and anchoring of the endoscope 104 thereto. Preferably, peripheral balloon 108 is a relatively soft, highly compliant balloon, operative to at least partially conform to the shape of the interior surface of the generally tubular body portion when in engagement therewith.

It is appreciated that peripheral balloon 108 may be formed of suitable well-known stretchable materials such as latex, flexible silicon, or highly flexible nylon. Alternatively, peripheral balloon 108 may be formed of polyurethane, which is less stretchable and conforming than latex, flexible silicon or highly flexible nylon. Preferably, the diameter of peripheral balloon 108 is sufficient to ensure tight anchoring at any part of the generally tubular body portion. Alternatively, peripheral balloon 108 may be obviated.

In accordance with one embodiment of the present invention, tubular sleeve 110 and peripheral balloon 108 may be produced from different materials. For example, sleeve 110 may be formed of very thin and very flexible polyurethane while balloon 108 is formed of nylon. Alternatively, sleeve 110 and balloon 108 may be produced from generally the same material but with different mechanical properties. For example, balloon 108 may be formed of a silicon material having width of 0.5 millimeter and hardness of approximately 50 shore D, whereas sleeve 110 may be formed of a silicone material having width of 0.3 millimeter and hardness of approximately 30 shore D. A preferred structure of sleeve 110 provides high bendability of the distal portion of endoscope 104 together with tubular sleeve 110. A preferred structure of balloon 108 provides firm anchoring of endoscope 104 to the generally tubular body portion when balloon 108 is in an inflated state.

In a preferred embodiment of the present invention, auxiliary assembly 106 may comprise at least one external tube 122. External tube 122 may be attached to the endoscope 104 at multiple locations along its length by any suitable conventional means such as medical adhesive tape or flexible bands 120. External tube 122 is preferably attached to tube 116 by a band 123. A proximal end 124 of tube 122 is typically open to enable a proximal end 125 of an inflation tube 126 coupled to a balloon 127 of an endoscope tool 128 to extend therefrom outside of a patient's body, thereby enabling insertion, removal and manipulation of tool 128 by an operator. Additionally any other suitable endoscope tool may be inserted, removed or manipulated through tube 122. Proximal end 125 of inflation tube 126 of endoscope tool 128 is also coupled to the inflation control assembly 115.

Many of the features of endoscope tool 128 are described in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

In accordance with a preferred embodiment of the present invention, useful for small intestine endoscopy, the diameter of balloon 127 when fully inflated is in the range of 35-45 mm. Preferably, inflation of the peripheral balloon 127 to a diameter less than 45 mm may be achieved using relatively low pressure, such as in the range of 30-70 millibars.

A distal end 129 of external tube 122 preferably extends slidably and telescopically through part of the length of a coil spring 130 which movably and slidably resides within a lumen 132, which preferably forms part of tubular sleeve 110. Preferably distal end 129 is beveled for ease of passage into and through coil spring 130. It is a particular feature of the present invention that spring 130 defines a generally non-collapsible and highly flexible channel for endoscope tool 128. It is a further particular feature of the present invention that lumen 132 has a generally saddle shaped cross section, as seen particularly at reference numeral 134, which is sufficiently wide to enable spring 130 to be slidably displaced laterally depending on the curvature of the endoscope 104. This enhances the flexibility of the combination of endoscope 104 and the auxiliary assembly 106. It is appreciated that although provision of spring 130 is preferred, spring 130 may be replaced by a suitable, flexible, non-collapsible tube of another type. In accordance with a preferred embodiment of the present invention, useful for small intestine endoscopy, the inner diameter of spring 130 is in the range of 3-6 mm. Preferably, balloon 127 when in a fully deflated state may assume a small enough cross section to allow its positioning at least partially within spring 130 if needed, for example during oral insertion of the flexible endoscope assembly through the stomach into the small intestine.

As illustrated in FIG. 1A, a distal end 136 of spring 130 is located adjacent to a first side wall 137 of lumen 132. Spring 130 extends generally diagonally along lumen 132 such that a proximal end 138 thereof lies adjacent a second side wall 139 of lumen 132, opposite to first side wall 137.

It is appreciated that during operation of the endoscopy system 100, when the endoscope 104 and the auxiliary endoscopy assembly 106 are curved in various directions, the orientation of spring 130, particularly proximal end 138 thereof, may change appropriately.

It is seen that spring 130 is preferably angularly misaligned with a respect to the central lumen 111. Generally diagonal orientation of spring 130 within lumen 132 is particularly useful in reducing, minimizing or eliminating substantial resistance of spring 130 to bending of endoscope 104 inserted within central lumen 111.

A forward collar element 140 preferably receives distal end 136 of coil spring 130 and removably connects it to a distal end 142 of tubular sleeve 110 and thus to a distal end 144 of endoscope 104 in press-fit frictional engagement. A stretchable band 146 preferably surrounds collar element 140 and presses it into frictional engagement with distal end 142 of tubular sleeve 110 and with distal end 144 of endoscope 104. It is appreciated that lumens 112 and 132 do not extend to distal end 142 of tubular sleeve 110 and thus are not engaged by collar element 140.

It is appreciated that the lumens 111, 112 and 132 may be formed integrally as part of tubular sleeve 110 in any appropriate manner, such as by extrusion, for example. Alternatively, any one or more of lumens 111, 112 and 132 may be formed as a separate tube and may be attached to tubular sleeve 110 in any suitable manner, such as by an adhesive.

In a preferred embodiment of the present invention, tubular sleeve 110 is approximately 120-200 mm in length and spring 130 is approximately 100-160 mm in length.

Preferably, the longitudinal distance between a distal edge of peripheral balloon 108 and the distal edge of tubular sleeve 110 does not exceed approximately 20 mm.

It is a particular feature of the present invention that a typical wall thickness of lumens 111, 112 and 132 of the tubular sleeve 110 is relatively thin, such as in the range of 0.15-0.7 mm, so as to provide enhanced flexibility of the tubular sleeve 110.

Preferably, for a typical endoscope diameter range of 10-13 mm, the circumference of central lumen 111 is preferably in the range of 31-41 mm, and its inner diameter is preferably 1-3 mm larger than the outer diameter of the endoscope.

In accordance with a preferred embodiment of the invention, inflation tube 126 includes a guide wire 150, which is preferably selectably bendable at one or more predetermined bending locations, here indicated in phantom lines by indentations 152. Guide wire 150 preferably terminates adjacent a distal end of balloon 127. Further in accordance with a preferred embodiment of the present invention, inflation tube 126 also includes a selectable steering wire 154, which extends beyond the proximal end of inflation tube 126, so as to be manipulatable by an operator for steering of the endoscope tool 128.

A distal end of selectable steering wire 154 is fixedly coupled to the guide wire 150 at an attachment location forwardly of one or more predetermined bending locations. The attachment location may be either interior of balloon 127 or forward thereof. Pulling on the selectable steering wire 154 causes bending of the guide wire 150 and corresponding steering of the endoscope tool 128.

It is appreciated that the structure of the inflation tube 126, including guide wire 150 and selectable steering wire 154, and the corresponding structure of the endoscope tool 128, although illustrated and described herein as an endoscope tool structure, is equally applicable to catheters generally, which may be employed without an endoscope.

Figure 2B:
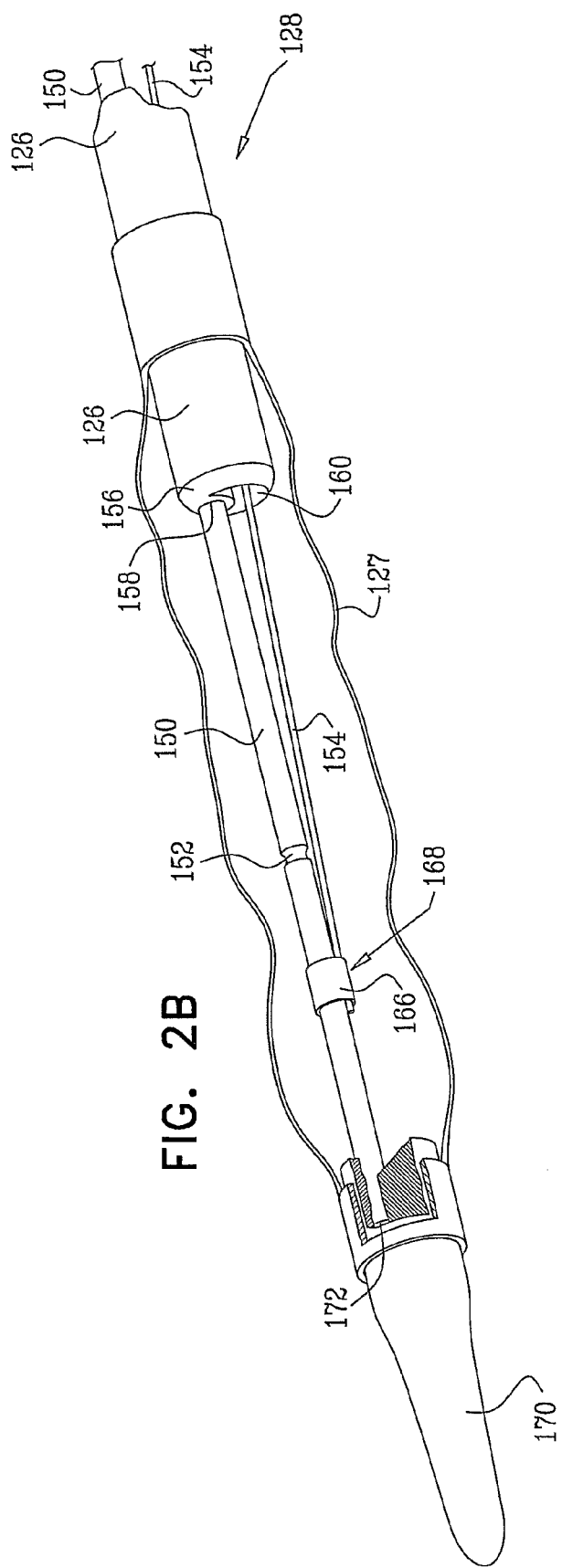

Reference is now made to FIGS. 2A and 2B, which are respective exploded and partially cut-away pictorial illustrations of a catheter or endoscope tool 128 and associated inflation tube 126 constructed and operative in accordance with a preferred embodiment of the present invention. As seen in FIGS. 2A & 2B, the inflation tube 126 terminates at a cap 156, which is attached at the interior of a distal end of inflation tube 126 and preferably includes at least two lumens, here designated by reference numerals 158 and 160. The guide wire 150 preferably extends through lumen 158 and is fixed to cap 156 thereat, while the selectable steering wire 154 preferably extends through lumen 160.

A collar 166 preferably fixedly attaches a distal end of selectable steering wire 154 to the guide wire 150 forwardly of at least one indentation 152. In this embodiment, the attachment location, designated by reference numeral 168, of the distal end of the selectable steering wire 154 to the guide wire 150 by collar 166 lies within balloon 127.

A distal end of the guide wire 150 preferably is fixed to a tip element 170, preferably within a recess 172 formed therein. Balloon 127 is sealingly fixed, at a proximal end thereof, onto a distal end of inflation tube 126 and, at a distal end thereof, onto a proximal end of tip 170.

Reference is now made to FIGS. 3A & 3B, which are sectional illustrations of the catheter or endoscope tool of FIGS. 2A & 2B in respective straight and bent operative steering orientations. FIG. 3A shows the catheter or endoscope tool extending along a longitudinal axis 174. It is seen that when selectable steering wire 154 is retracted relative to cap 156, as indicated by arrow 176, it applies a pulling force to a distal portion 178 to the guide wire 150 forward of indentation 152, causing distal portion 178 and tip element 170 to rotate in a direction indicated by arrow 180 relative to longitudinal axis 174. Preferably the guide wire 150 is sufficiently resilient under such bending so as to return to its axial orientation shown in FIG. 3A once selectable steering wire 154 is released.

It is appreciated that torque may be applied to tube 126 and/or guide wire 150, thereby allowing an operator to rotate balloon 127 with tip element 170 around axis 174 during in vivo inspection of a tubular body portion, such as described in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

Figure 4A:
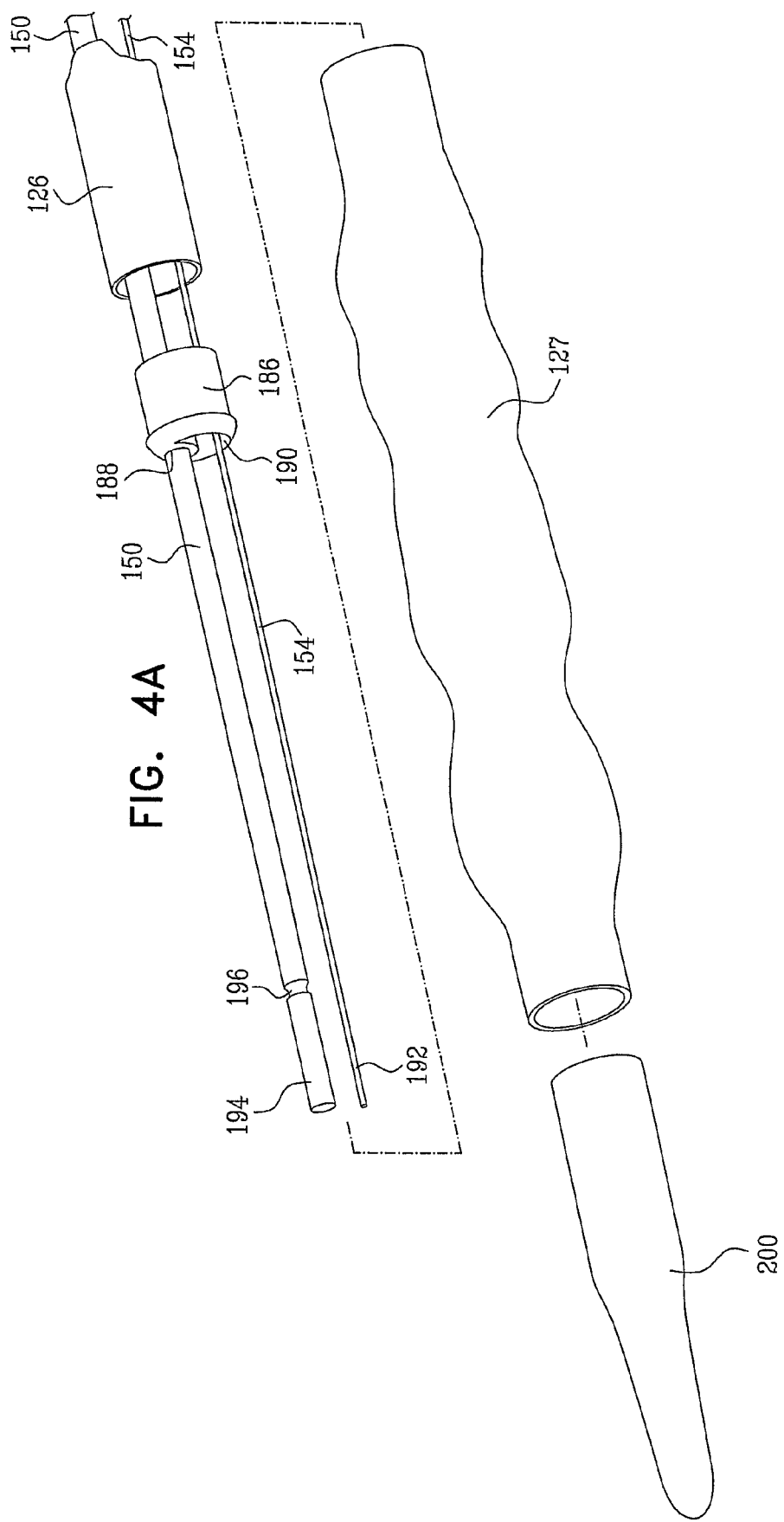
FIGS. 4A and 4B are respective exploded and partially cut-away pictorial illustrations of a catheter or endoscope tool and associated inflation tube, constructed and operative in accordance with another preferred embodiment of the present invention.
Figure 4B:
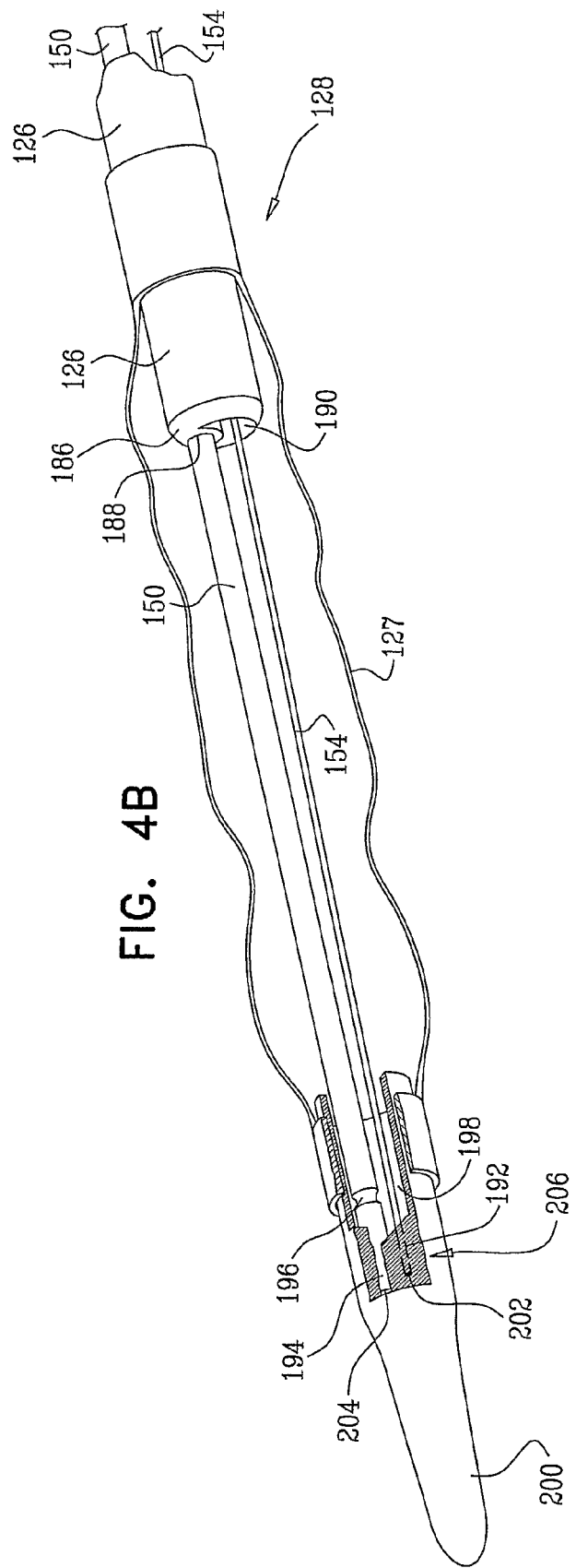

Reference is now made to FIGS. 4A and 4B, which are respective exploded and partially cut-away pictorial illustrations of a catheter or endoscope tool 128 and associated inflation tube 126 constructed and operative in accordance with another preferred embodiment of the present invention. As seen in FIGS. 4A & 4B, the inflation tube 126 terminates at a cap 186, which is attached at the interior of a distal end of inflation tube 126 and preferably includes at least two lumens, here designated by reference numerals 188 and 190. The guide wire 150 preferably extends through lumen 188 and is fixed to cap 186 thereat, while the selectable steering wire 154 preferably extends through lumen 190.

A distal end 192 of selectable steering wire 154 is attached to a distal end 194 of guide wire 150 forwardly of at least one indentation 196, which here is located forwardly of balloon 127 in a recess 198 formed in a tip element 200. In this embodiment, the attachment of the distal end 192 of selectable steering wire 154 to the distal end 194 of guide wire 150 is realized by fixedly attaching distal ends 192 and 194 to the tip element 200, within respective recesses 202 and 204, and the attachment location, designated by reference numeral 206, lies within tip element 200. Balloon 127 is sealingly fixed, at a proximal end thereof, onto a distal end of inflation tube 126 and, at a distal end thereof, onto a proximal end of tip 200.

Figure 5A:
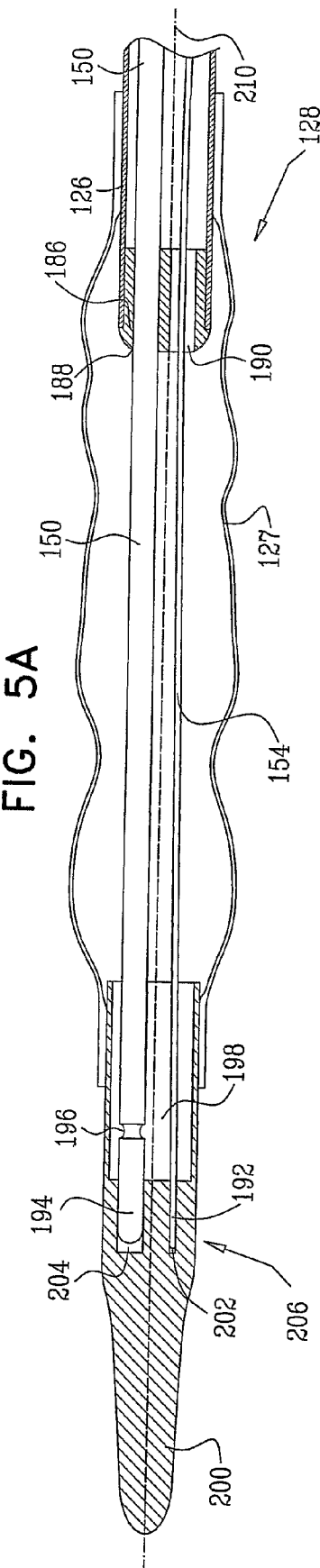
FIGS. 5A and 5B are sectional illustrations of the catheter or endoscope tool of FIGS. 4A & 4B in respective straight and bent operative steering orientations.
Figure 5B:
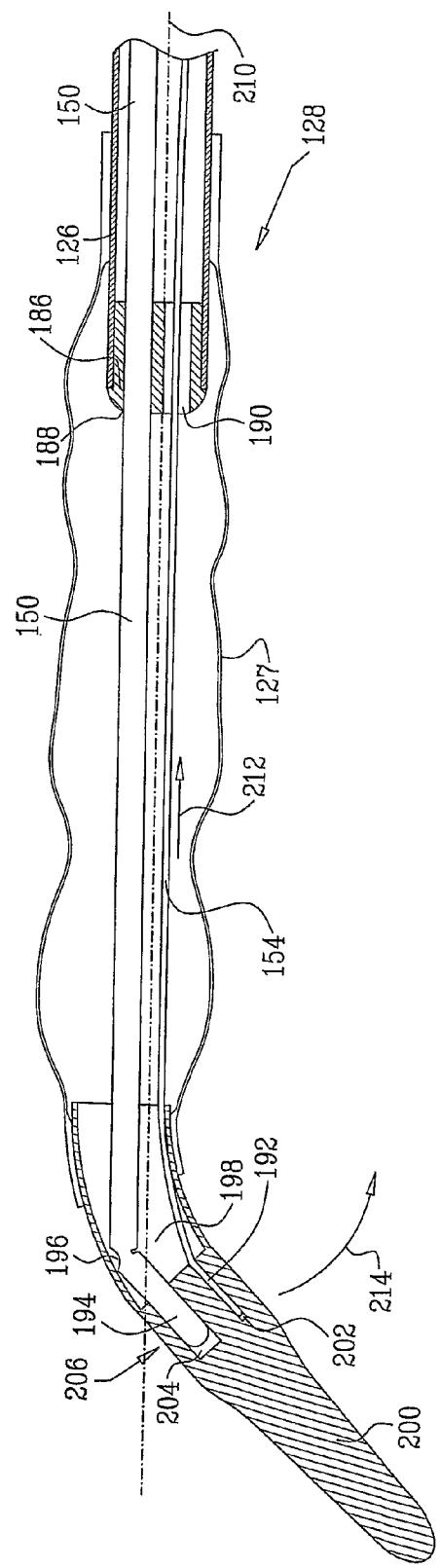

Reference is now made to FIGS. 5A & 5B, which are sectional illustrations of the catheter or endoscope tool of FIGS. 4A & 4B in respective straight and bent operative steering orientations. FIG. 5A shows the catheter or endoscope tool extending along a longitudinal axis 210. As seen in FIG. 5B, when selectable steering wire 154 is retracted relative to cap 186, as indicated by arrow 212, it applies a pulling force to distal end 194 of the guide wire 150 forward of indentation 196, causing distal portion 194 and tip element 200 to rotate in a direction, indicated by arrow 214, relative to longitudinal axis 210. Preferably, the guide wire 150 is sufficiently resilient under such bending so as to return to its axial orientation shown in FIG. 5A once selectable steering wire 154 is released.

It is appreciated that torque may be applied to tube 126 and/or guide wire 150, thereby allowing an operator to rotate balloon 127 with tip element 200 around axis 210 during in vivo inspection of a tubular body portion, such as described in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

Figure 6A:
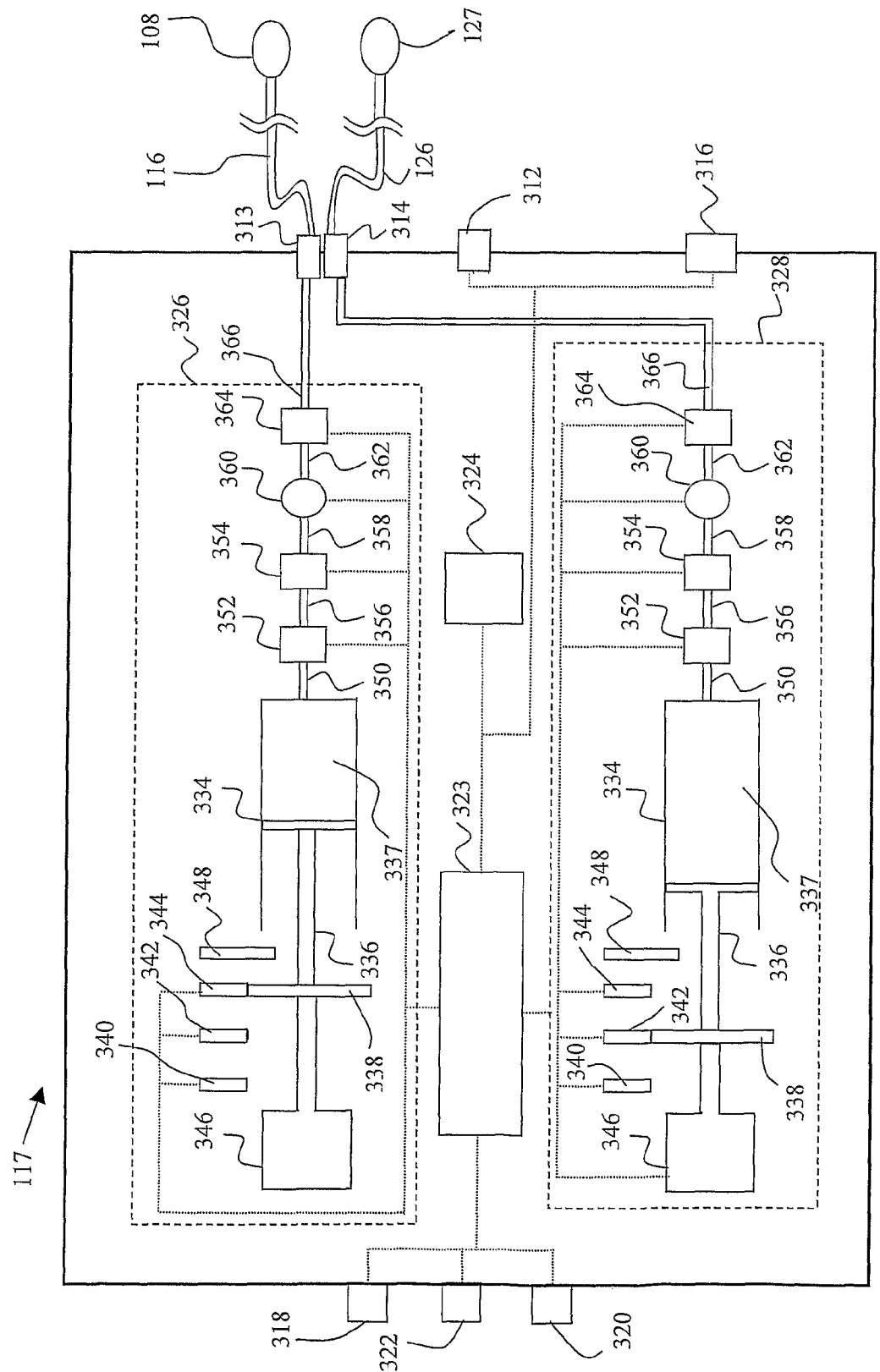
FIGS. 6A, 6B and 6C are simplified schematic illustrations of an inflation control unit forming part of the flexible endoscope system of FIGS. 1A and 1B in three different operative orientations.
Figure 6B:
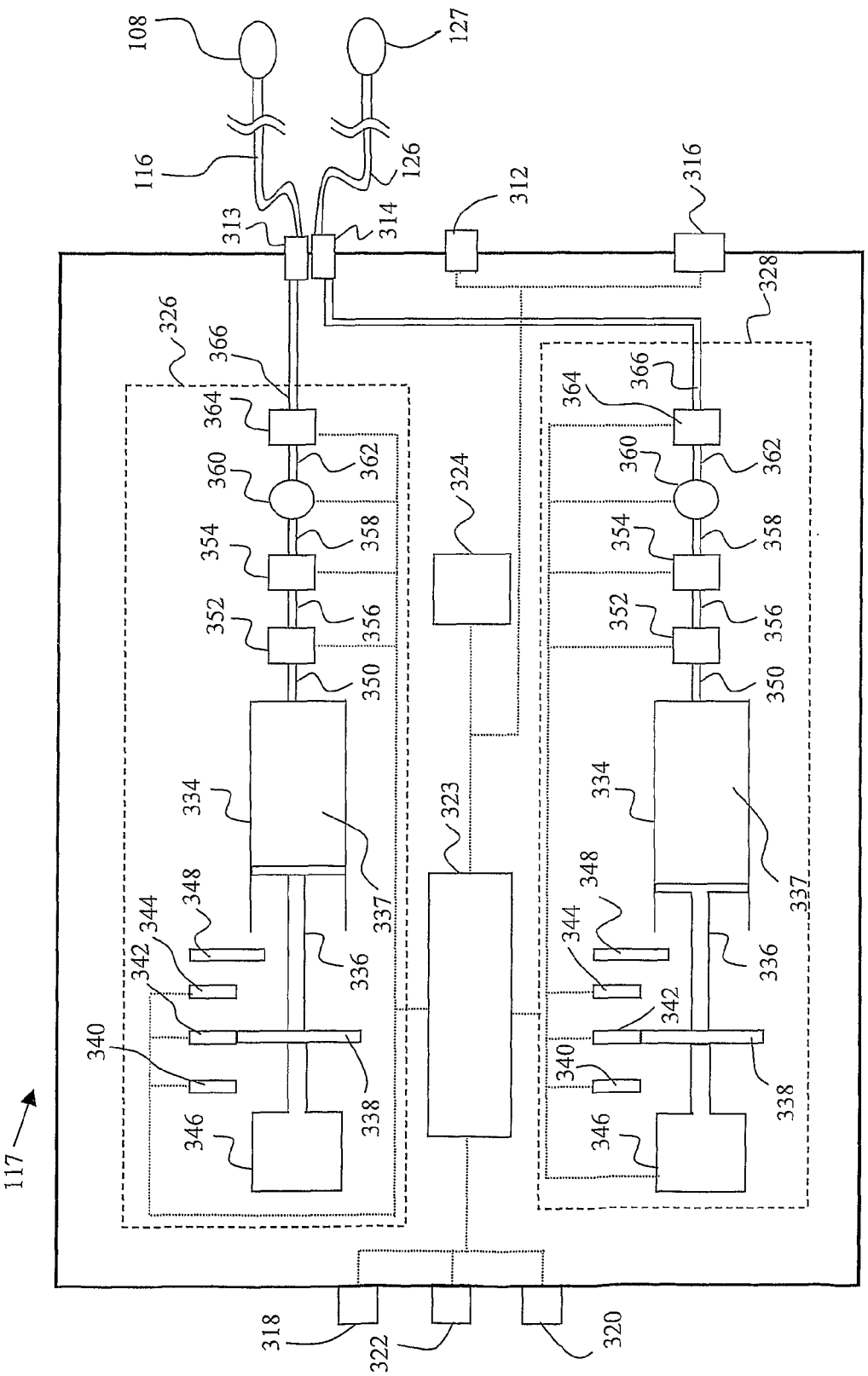
Figure 6C:
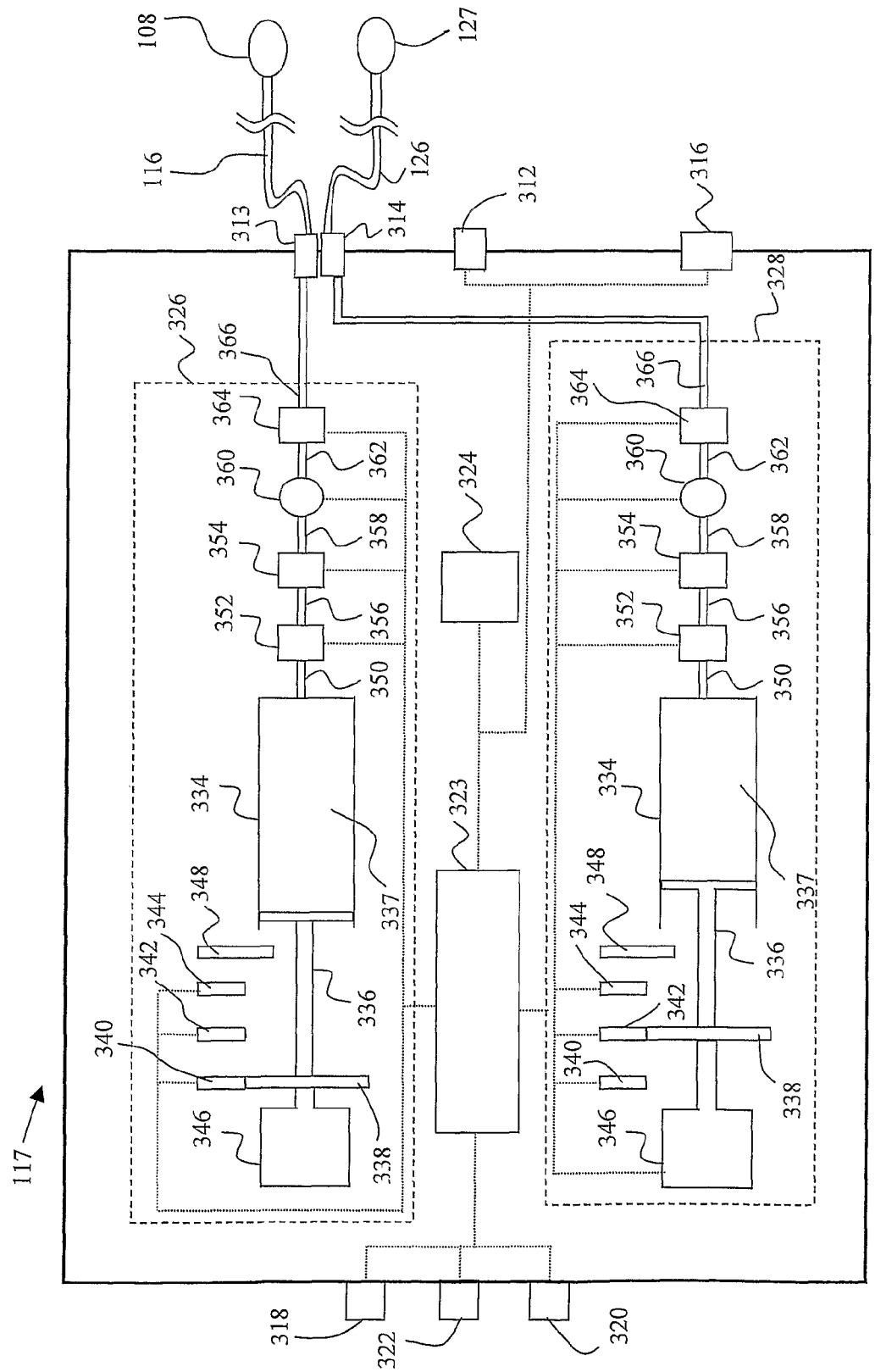

Reference is now made to FIGS. 6A, 6B and 6C, which are simplified schematic illustrations of control unit 117 of inflation control assembly 115 of the flexible endoscope system of FIGS. 1A and 1B in three different operative orientations.

In a preferred embodiment of the present invention, the inflation control assembly 115 is constructed and operative to facilitate the pneumatic inflation and/or deflation of balloons 108 and 127, which are coupled thereto by respective tubes 116 and 126.

Control unit 117 of inflation control assembly 115 is preferably an electro-mechanically operative pneumatic control subassembly which includes on its front panel a power on/off switch 312, connectors 313 and 314, for respective tubes 116 and 126, preferably female-type pneumatic connectors, and a buzzer mute switch 316.

FIGS. 6A-6C each also illustrate a foot pedal electrical connector 318, an indicator panel electrical connector 320, and a power supply electrical connector 322, all of which are preferably female-type electrical connectors.

Specific reference is now made to FIG. 6A, which is a simplified schematic illustration of the control unit 117 in an ambient inflation pressure operational state. As seen in FIG. 6A, the control unit 117 includes, in addition to the various connectors and switches described hereinabove, an electronic controller 323, a buzzer 324, and two identical inflator/deflator assemblies, respectively indicated by reference numerals 326 and 328. The electronic controller 323 is an electronic circuit which includes software that receives inputs from various components of the inflation control assembly 115 and activates various components of the inflation control assembly 115 in a manner which is described hereinbelow with reference to FIGS. 7A-7D.

Inflator/deflator assemblies 326 and 328 each include a variable volume air reservoir 334 which is coupled in a closed circuit with a corresponding balloon 108 or 127 via a corresponding tube 116 or 126. A piston 336 is movable within each air reservoir 334 to thereby vary the air volume 337 of the air reservoir 334. Associated with each piston 336 is a flange 338 arranged such that, during the axial movement of piston 336, flange 338 may be located adjacent a deflated balloon status sensor 340, an ambient balloon status sensor 342 and an inflated balloon status sensor 344. Each of sensors 340, 342 and 344 detects the proximity of flange 338 and provides a corresponding output to controller 323, indicating the corresponding volume of the air volume 337 and thus the inflation/deflation status of a corresponding balloon. Sensors 340, 342 and 344 may be any suitable type of proximity sensors, such as optical sensors or capacitive sensors. An example of an appropriate sensor type is EE-SX672R, manufactured by Omron of Japan.

Piston 336 is driven linearly by a motor 346 moved inwardly or outwardly of air reservoir 334, thereby respectively decreasing or increasing the air volume 337. The operation of motor 346 is controlled by controller 323. Motor 346 may be any suitable electric motor, such as a linear motor, a rotary motor or a step motor.

A mechanical stop 348 prevents the movement of piston 336 beyond a predefined distance, by physically engaging flange 338. This limitation provides a limit on the pressure within air reservoir 334, due to the limited decrease of the air volume 337 in air reservoir 334.

Air reservoir 334 is pneumatically connected, via a first intermediate air tube 350, to a valve 352 that has two states. An example of a suitable purging valve 352 is a solenoid valve G80-24V/DC 6.5 W TWO WAY NO 1.6 mm, manufactured by Baccara of Israel. When the valve 352 is a first state, it allows air flow via first intermediate air tube 350 between air reservoir 334 and the ambient atmosphere. When 352 is in a second state, air flowing via the first intermediate air tube 350 communicates via valve 352, a balloon valve 354, and a second intermediate air tube 356 with a corresponding balloon 108 or 127 (FIGS. 1A & 1B).

Balloon valve 354 is typically a solenoid valve G80-24V/DC 6.5 W TWO WAY NO 1.6 mm, manufactured by Baccara of Israel. Balloon valve 354 may be in either one of two states; an open state and a closed state. When the balloon valve 354 is in the open state, air flowing in second intermediate air tube 356 can pass via the balloon valve 354 to a third intermediate air tube 358. When balloon valve 354 is open, third intermediate air tube 358 couples air from second intermediate air tube 356 via balloon valve 354 to a pressure sensor 360.

Pressure sensor 360 detects the air pressure in the third intermediate air tube 358. The output of pressure sensor 360 may be used by controller 323 to govern the operation of the valve 352 and of the balloon valve 354. An example of pressure sensor 360 is sensor number 6763, manufactured by Hegra Electric Ltd, Northern Way, Bury St. Edmunds, Suffolk IP32 6NN, United Kingdom.

It is appreciated that the output of pressure sensor 360 may be employed by the controller 323 for actuation of balloon valve 354, valve 352 and piston 336. It is appreciated that actuation of the above described pneumatic components may be different for different levels of pressure or vacuum which are indicated by pressure sensor 360. It is appreciated that pressure sensor 360 may comprise multiple pressure sensors, each of which may provide a digital input of a single pressure value. For instance, detection of pressure higher than 60 mbar by pressure sensor 360 may cause balloon valve 354 to be in its closed state. Detection of pressure that is below 60 mbar by the pressure sensor 360 may cause balloon valve 354 to be in its open state. Similarly, detection of a vacuum level lower than −100 mbar by pressure sensor 360 may cause the balloon valve 354 to be in its closed state.

A fourth intermediate air tube 362 allows air flow from air tube 358 via pressure sensor 360 to an overpressure release valve 364. Release valve 364 has two states, an open and a closed state. In the closed state, release valve 364 allows air flow from fourth intermediate air tube 362 to a fifth intermediate air tube 366. In the open state, release valve 364 directs the air flow from fourth intermediate air tube 362 to the ambient atmosphere. Release valve 364 is in its closed state as long as the pressure within air tube 362 is below a predefined value. Whenever the pressure in air tube 362 exceeds the predefined value, the release valve 364 is automatically shifted to its open state.

This ensures that the pressure in a fifth intermediate air tube 366 and any components connected thereto outside of the control unit 117 (FIG. 1A), does not exceed the predefined pressure value set for release valve 364, corresponding to a safe, predefined value, such as 120 mbar. The transition of the release valve 364 from its closed to its open state may be automatic as in release valve 559B-1M-1.0 psi, manufactured by Circle Seal Controls, Inc., 2301 Wardlow Circle, Corona, Calif. 92880, USA.

It is appreciated that the release valve 364 may also be controlled by a backup control mechanism.

Each intermediate air tube 366 is connected to a corresponding one of tubes 116 and 126 (FIG. 1A) via a corresponding one of connectors 313 and 314.

It is appreciated that inflator/deflator assemblies 326 and 328 can be operated using identical components and by implementing the same or different algorithms, such that, for example balloon 108 may operate at a maximum inflation of 60 mbar, while balloon 127 may operate at a maximum inflation of 90 mbar.

Reference is now made additionally to FIGS. 7A-7D, which are simplified flow charts illustrating preferred modes of operation of the inflation control assembly 115 of FIGS. 6A-6C. An indicated above, control of the operation of inflation control assembly 115 is provided principally by controller 323 based on various sensor inputs, described hereinabove.

It is appreciated that the implementation of controller 323 may involve any suitable technology, for example, the use of embedded firmware, loading software from a digital memory device and loading software from an external source.

FIGS. 7A and 7B illustrate initialization functionality which is performed automatically once the power switch 312 is switched to its on state. A primary purpose of the initialization functionality is to ensure that, whatever is the initial state of the control unit 117 (FIG. 1A), prior to operation, balloons 108 and 127 are in their fully deflated (vacuum) operational states.

As seen in FIGS. 7A and 7B, following powering on of the inflation control assembly 115 (FIG. 1A), indication lights on panel 119 (FIG. 1A) blink, foot pedals 118 are disabled and buzzer 324 (FIGS. 6A-6C) sounds.

At this stage, initialization of one of the two identical inflator/deflator assemblies 326 and 328 begins. Once initialization of one of the identical inflator/deflator assemblies is completed, initialization of the other of the identical inflator/deflator assemblies takes place. In the illustrated example, initialization of inflator/deflator assembly 326 occurs first, starting with closing of balloon valve 354 and opening of valve 352 thereof. After a predetermined period of time, typically 210 ms, piston 336 is positioned by motor 346 such that flange 338 is adjacent inflated balloon status sensor 344. This is the state illustrated by FIG. 6A.

The balloon valve 354 is then opened and valve 352 is closed. Following a predetermined time duration, typically 210 ms, piston 336 is moved by motor 346 such that flange 338 is adjacent ambient balloon status sensor 342. This is the state illustrated by FIG. 6B.

Following a further predetermined time duration, typically 4 seconds, valve 352 is opened. Following an additional predetermined time duration, typically 3 seconds, valve 352 is closed.

Following a still further predetermined time duration, typically 210 ms, piston 336 is moved by motor 346 such that flange 338 is adjacent deflated balloon status sensor 340. This is the state illustrated by FIG. 6C.

Following yet another predetermined time duration, typically four seconds, balloon valve 354 is closed. This completes initialization of inflator/deflator assembly 326 and is followed by initialization of inflator/deflator assembly 328, which includes identical steps to those described above for initialization of inflator/deflector assembly 326.

Following completion of initialization of inflator/deflator assemblies 326 and 328, the indication lights on panel 119 (FIG. 1A) stop blinking and foot pedals 118 are enabled. At this stage, two vacuum indication lights, here designated by reference numerals 370 and 372 (FIG. 1A) are illuminated to indicate the presence of vacuum in balloons 108 and 127 (FIG. 1A).

Figure 7C:
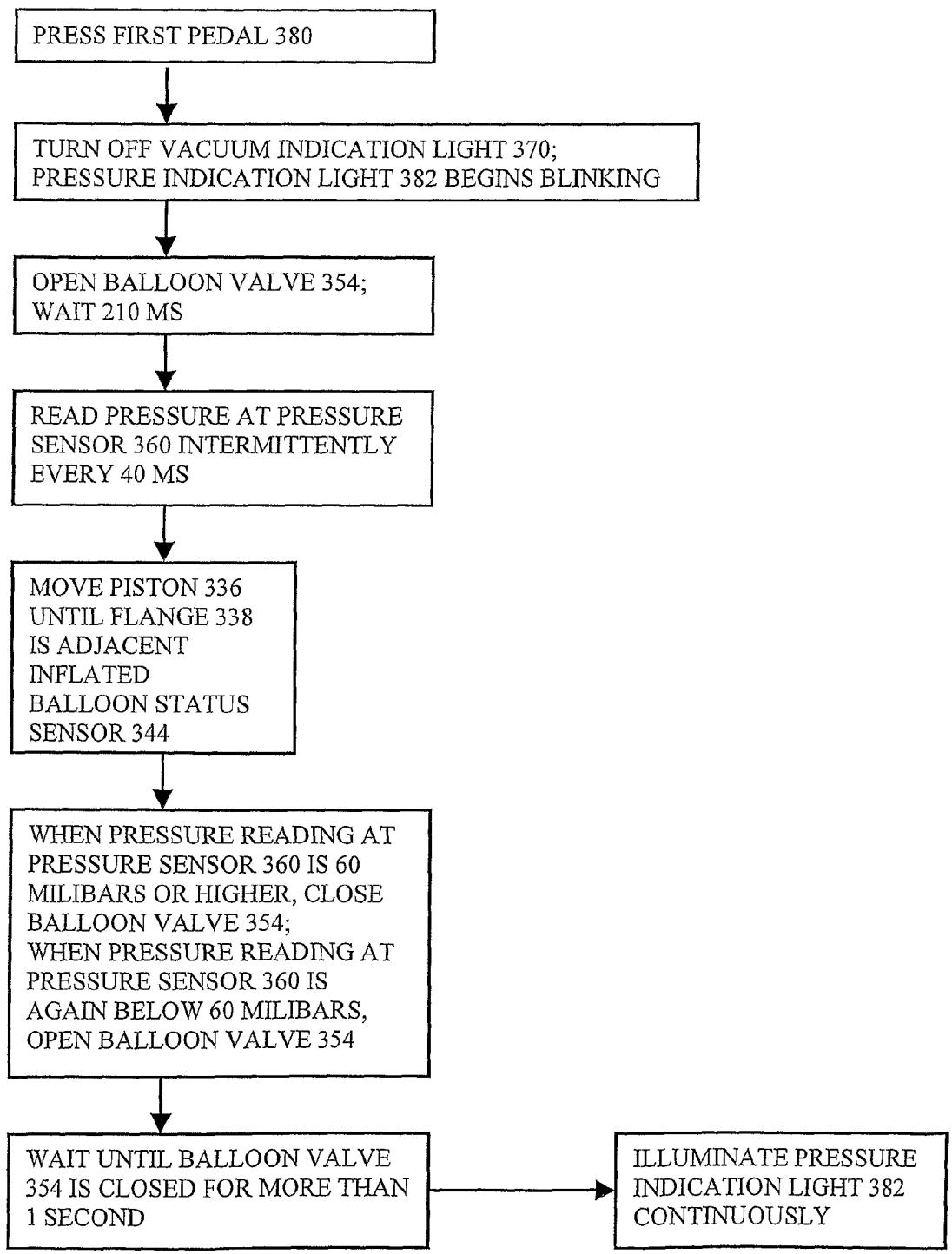

At this stage, normally inflation of one of balloons 108 and 127 takes place. Usually, but not necessarily, inflation of balloon 108 takes place first. As seen in FIG. 7C, inflation of balloon 108 is initiated by an operator pressing on one of the foot pedals 118, here designated by reference numeral 380, to send a signal to controller 323 (FIGS. 6A-6C) to initiate inflation of balloon 108. Indication light 370 is extinguished and another one of the indication lights on panel 119, a pressure indication light for balloon 108, here designated by reference numeral 382 (FIG. 1A), begins blinking. Balloon valve 354 is opened. Following a predetermined time duration, typically 210 ms, piston 336 is positioned by motor 346 such that flange 338 is adjacent inflated balloon status sensor 344. This is the state illustrated by FIG. 6A.

At this stage, piston 336 is pressurized to a relatively high pressure, typically 200 mbar and the desired pressure at balloon 108 is typically 60 mbar. Inflation of the balloon 108 is accomplished by intermittently opening and closing balloon valve 354 and monitoring the pressure at sensor 360, which is connected in series between piston 336 and balloon 108. When the desired pressure at sensor 360 remains steady at 60 mbar for at least a predetermined time, typically one second, balloon valve 354 remains closed and inflation of balloon 108 is considered to be completed and indicator light 382 is illuminated continuously. Even following completion of inflation of balloon 108, sensor 360 continues to monitor the pressure and if and when necessary, balloon valve 354 may be opened to top up the pressure at balloon 108.

Inflation of balloon 127 is initiated by an operator pressing on one of the foot pedals 118, here designated by reference numeral 384, to send a signal to controller 323 (FIGS. 6A-6C) to initiate inflation of balloon 127. Indication light 372 is extinguished and another one of the indication lights on panel 119, a pressure indication light for balloon 108, here designated by reference numeral 386 (FIG. 1A), begins blinking. Balloon valve 354 is opened. Following a predetermined time duration, typically 210 ms, piston 336 is positioned by motor 346 such that flange 338 is adjacent inflated balloon status sensor 344.

At this stage, piston 336 is pressurized to a relatively high pressure, typically 200 mbar and the desired pressure at balloon 127 is typically 60 mbar. Inflation of the balloon 127 is accomplished by intermittently opening and closing balloon valve 354 and monitoring the pressure at sensor 360, which is connected in series between piston 336 and balloon 127. When the desired pressure at sensor 360 remains steady at 60 mbar for at least a predetermined time, typically one second, balloon valve 354 remains closed and inflation of balloon 127 is considered to be completed and indicator light 386 is illuminated continuously. Even following completion of inflation of balloon 127, sensor 360 continues to monitor the pressure and if and when necessary, balloon valve 354 may be opened to top up the pressure at balloon 127.

Figure 7D:
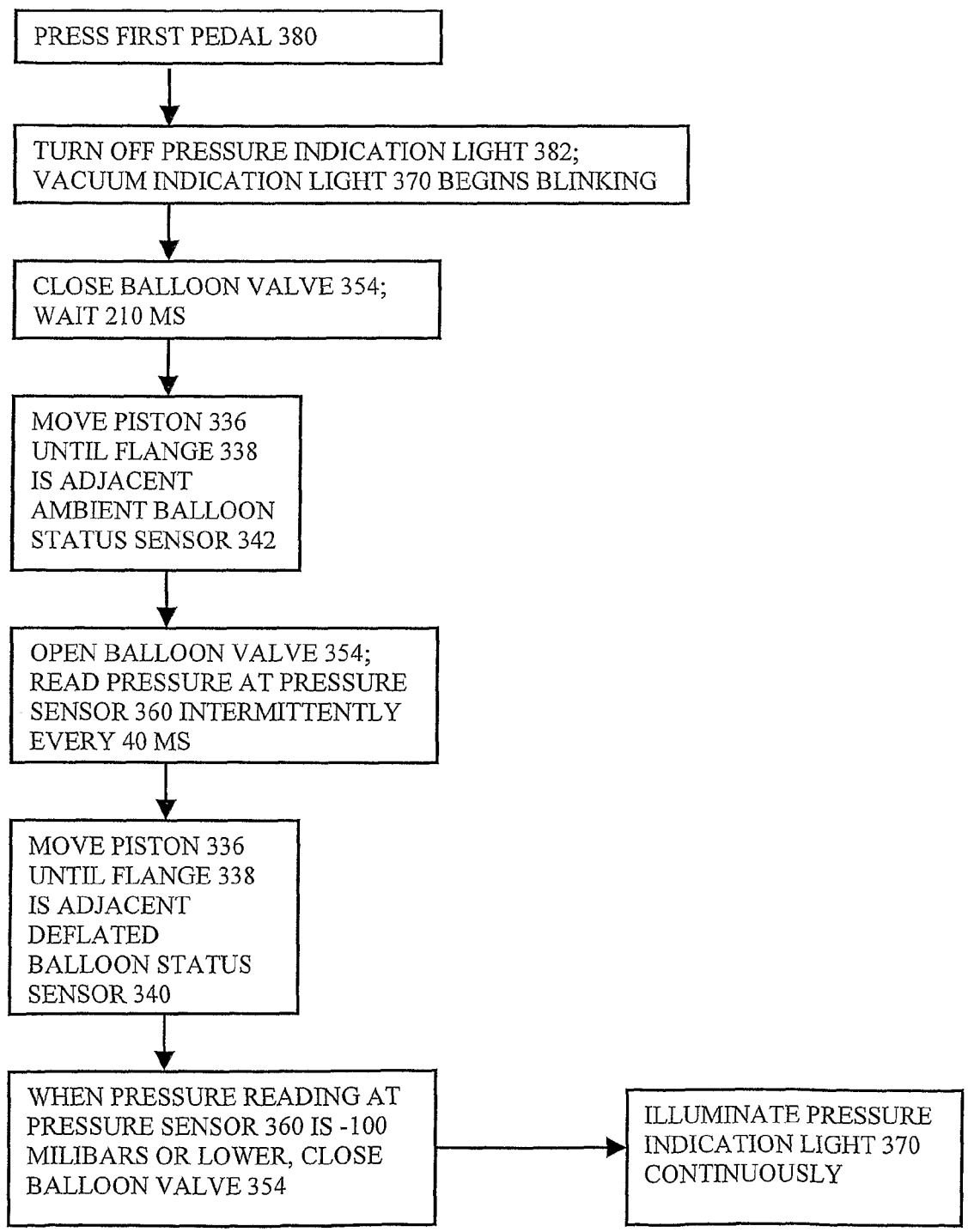

As seen in FIG. 7D, deflation of balloon 108 takes place by an operator pressing on foot pedal 380, to send a signal to controller 323 (FIGS. 6A-6C) to initiate deflation of balloon 108. Indication light 382 is extinguished and vacuum indication light 370 begins blinking. Balloon valve 354 is closed. Following a predetermined time duration, typically 210 ms, piston 336 is positioned by motor 346 such that flange 338 is adjacent ambient balloon status sensor 342 and balloon valve 354 is opened. This is the state illustrated by FIG. 6B.

At this stage, piston 336 is at approximately ambient pressure. Piston 336 is then positioned by motor 346 such that flange 338 is adjacent deflated balloon status sensor 340. This is the state illustrated by FIG. 6C.

Deflation of the balloon 108 is accomplished by monitoring the pressure at sensor 360. When the desired pressure at sensor 360 reaches a negative level of −100 mbar, balloon valve 354 is closed, deflation of balloon 108 is considered to be completed and indicator light 370 is illuminated continuously. Even following completion of deflation of balloon 108, sensor 360 continues to monitor the pressure inside balloon 108.

Deflation of balloon 127 takes place by an operator pressing on foot pedal 384, to send a signal to controller 323 (FIGS. 6A-6C) to initiate deflation of balloon 127. Indication light 386 is extinguished and vacuum indication light 372 begins blinking. Balloon valve 354 is closed. Following a predetermined time duration, typically 210 ms, piston 336 is positioned by motor 346 such that flange 338 is adjacent ambient balloon status sensor 342 and balloon valve 354 is opened. This is a state corresponding to the state illustrated in FIG. 6B.

At this stage, piston 336 is at approximately ambient pressure. Piston 336 is then positioned by motor 346 such that flange 338 is adjacent deflated balloon status sensor 340.

Deflation of the balloon 127 is accomplished by monitoring the pressure at sensor 360. When the desired pressure at sensor 360 reaches a negative level of −100 mbar, balloon valve 354 is closed, deflation of balloon 127 is considered to be completed and indicator light 372 is illuminated continuously. Even following completion of deflation of balloon 127, sensor 360 continues to monitor the pressure inside balloon 127.

One of the indicator lights on panel 119 may be a failure indication light, here designated by reference numeral 390. This light may be illuminated when any of the functionalities described above fails to be fully performed.

Reference is now made to FIGS. 8A and 8B, which are simplified partially cut-away illustrations of a balloon catheter 399 constructed and operative in accordance with a preferred embodiment of the present invention. As seen in FIGS. 8A & 8B, the balloon catheter of the present invention preferably comprises an inflation tube 400 which terminates at a cap 402, which is attached at the interior of a distal end of inflation tube 400 and preferably includes at least two lumens, here designated by reference numerals 404 and 406. A guide wire 410 preferably extends through lumen 404 and is fixed to cap 402 thereat, while lumen 406 is open for balloon inflation and deflation.

A distal end of the guide wire 410 preferably is fixed to a tip element 412, preferably within a recess 414 formed therein. A balloon 420 is sealingly fixed, at a proximal end thereof, onto a distal end of inflation tube 400 and, at a distal end thereof, onto a proximal end of tip 412.

FIG. 8A shows balloon 420 in a non-inflated, ambient state wherein the walls of the balloon 420 are nearly taut but not appreciably tensioned. In this orientation, the guide wire 410 extends along an axis 421 generally parallel to and spaced from longitudinal axis 422 of the inflation tube 400, cap 402 and tip 412. FIG. 8B shows balloon 420 in a fully-inflated state, typically at a pressure of approximately 20-100 millibars. It is seen that inflation of balloon 420 causes guide wire 410 to be bowed in a preferably predetermined direction with respect to axis 422, which direction is determined at least partially by the spatial relationship between axes 421 and 422, and to an extent which is a predetermined function of the amount of inflation, thus resulting in a somewhat asymmetric, off-axis, inflated balloon configuration as seen.

According to a preferred embodiment of the present invention, the length of balloon 420 in its non-inflated, ambient state (FIG. 8A) is approximately 40-100 millimeters, and the length of balloon 420 in its fully-inflated state (FIG. 8B) is approximately 30-80 millimeters. In a specific configuration balloon 420, in its non-inflated, ambient state, has a length of 80-95 millimeters, the corresponding length of balloon 420 in its fully-inflated state is 60-75 millimeters, and the diameter of balloon 420 in its fully-inflated state is 30-45 millimeters.

It is appreciated that the angle between the longitudinal axis of tip element 412 and axis 422 in the fully-inflated state (FIG. 8B) may be typically greater than 30 degrees, and may be approximately 90 degrees or more in the specific configuration of balloon 420 described hereabove. According to a preferred embodiment of the present invention, the angle between the longitudinal axis of the tip element 412 and axis 422 in the fully-inflated state is in the range of 40-75 degrees. Alternatively, the angle between the longitudinal axis of the tip element 412 and axis 422 in the fully-inflated state is in the range of 75-110 degrees.

It is appreciated that torque may be applied to tube 400 and/or guide wire 410, thereby allowing an operator to rotate balloon 420 with tip element 412 around axis 422 during in vivo inspection of a tubular body portion, such as described in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

It is appreciated that inflation pressure in the range of 45-100 millibars may be suitable for anchoring the inflated balloon 420 and thus the balloon catheter to an generally tubular body portion to be inspected or treated, such as the intestine, as described for example in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

It is appreciated that a generally higher inflation pressure may be applied to balloon 420, as suitable. It is appreciated that guide wire 410 is sufficiently flexible to allow its bending during inflation of balloon 420 and to allow balloon 420 to be fully inflated when appropriate inflation pressure is applied.

As seen in FIGS. 8A and 8B, inflation tube 400 protrudes into the internal volume of balloon 420 to a certain extent. In a preferred embodiment of the present invention, tube 400 protrudes between 7 to 20 millimeters into the internal volume of balloon 420. It is appreciated that protrusion of inflation tube 400 into the internal volume of balloon 420 is useful for preventing or reducing blockage of inflation lumen 406 by balloon 420 in case of twisting of balloon 420 around axis 422 while being inflated.

Reference is now made to FIGS. 9A, 9B, 9C, 9D, 9E and 9F, which are simplified, partially cut away, partially sectional, illustrations of the operation of the apparatus of FIGS. 8A & 8B.

Figure 9A:
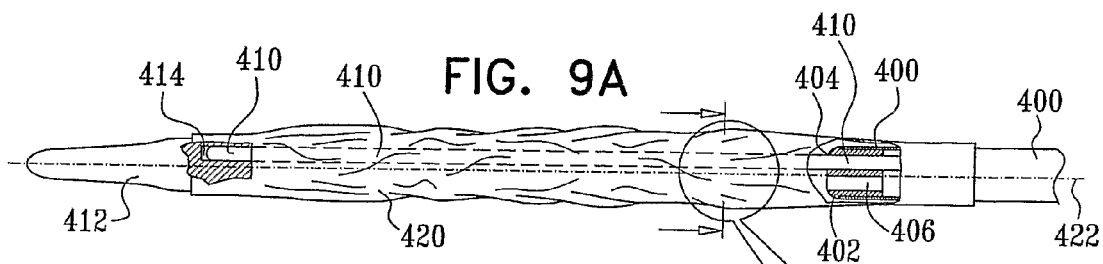
FIGS. 9A, 9B, 9C, 9D, 9E and 9F are simplified, partially cut away, partially sectional, illustrations of the operation of the apparatus of FIGS. 8A and 8B.

FIG. 9A illustrates the application of a partial vacuum, typically about −100 millibars, to the interior of balloon 420 via inflation tube 400 and lumen 406 of cap 402. It is appreciated that due to the nearly taut, but not appreciably tensioned, arrangement of the balloon 420, as described hereinabove with reference to FIG. 8A, the maximum cross-sectional diameter of the balloon catheter, as indicated at reference numeral 430, is relatively small, such as in the range of 2-4 millimeters, and preferably less than 3 mm, and is thus suitable for passage through an instrument channel of a conventional endoscope.

Figure 9B:
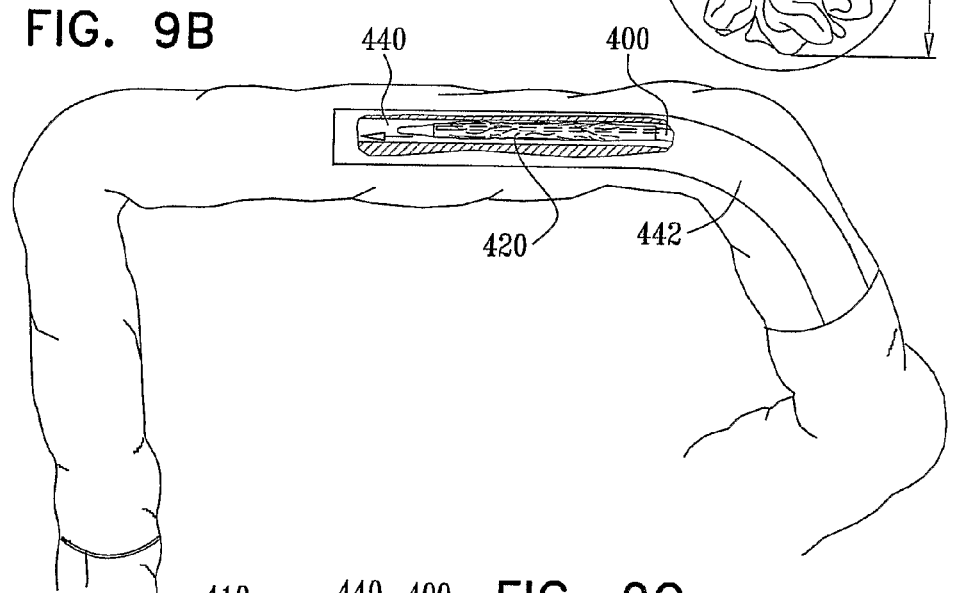

FIG. 9B illustrates the balloon catheter of FIGS. 8A-9A located in an instrument channel 440 of a conventional endoscope 442, located within the intestines of a patient.

Figure 9C:
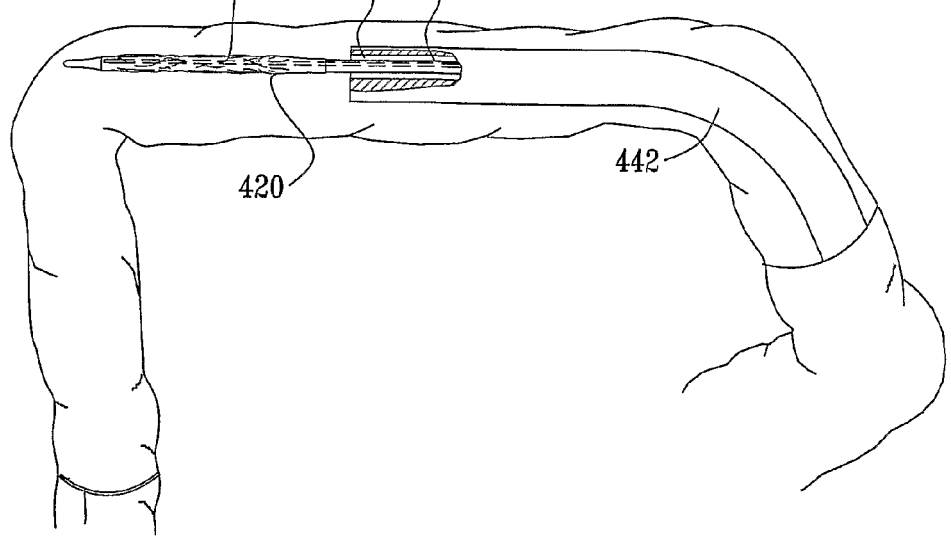
Figure 9D:
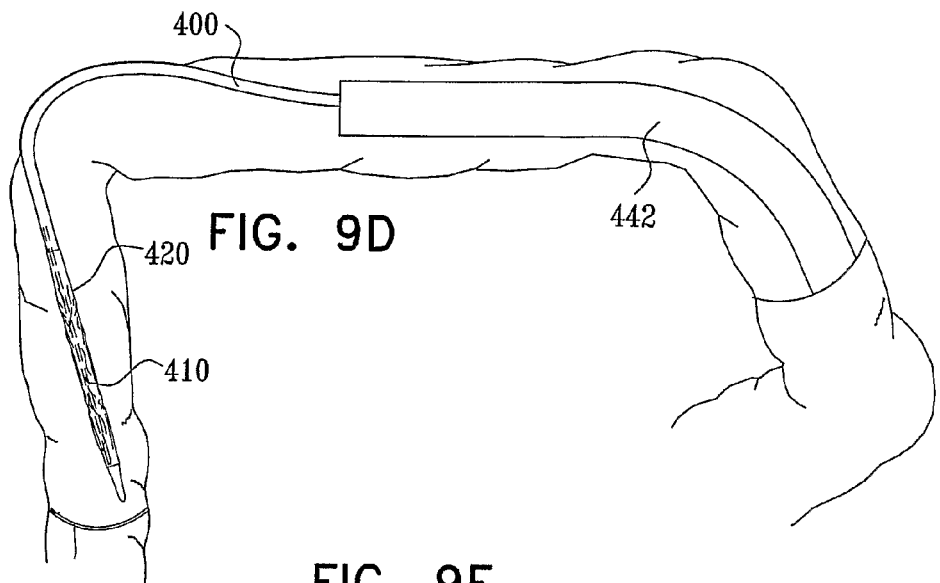
Figure 9E:
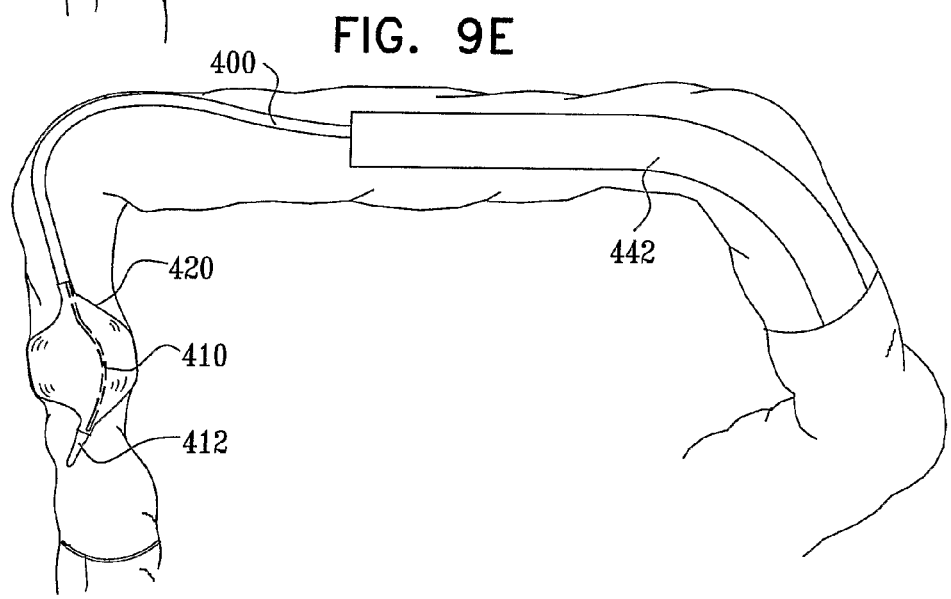

FIG. 9C illustrates the balloon catheter of FIGS. 8A-9B emerging from instrument channel 440. FIG. 9D illustrates the balloon catheter of FIGS. 8A-9B located at an anchoring location forward of the end of the endoscope 442. FIG. 9E illustrates the balloon catheter of FIGS. 8A-9C fully inflated at the anchoring location. It is seen that the guide wire 410 is bowed and thus the balloon 420 is generally asymmetric due to the inflation, as described above.

Figure 9F:
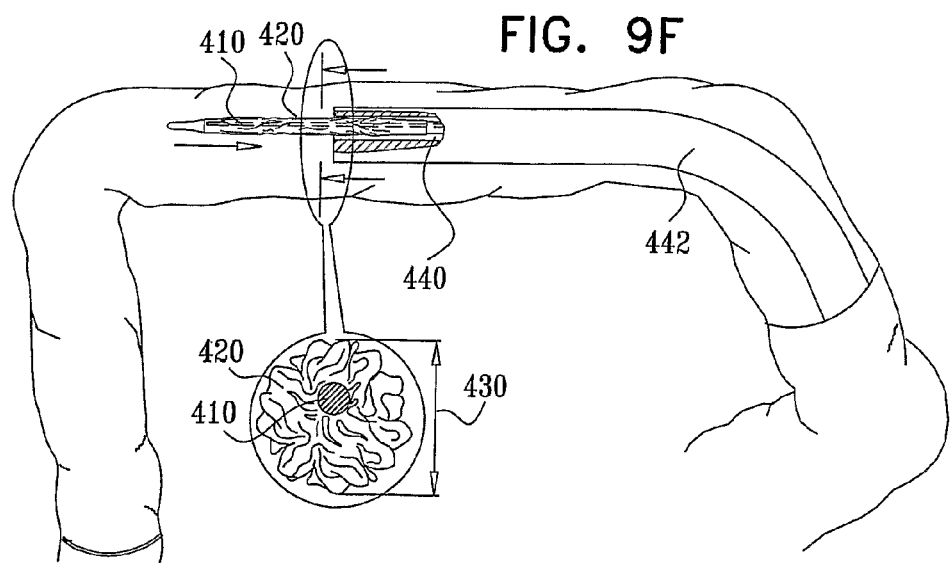

FIG. 9F illustrates deflation of the balloon 420 by application of a partial vacuum, typically about −100 millibars, to the interior of balloon 420 via inflation tube 400 and lumen 406 of cap 402 and reinsertion thereof into instrument channel 440, for removal from the patient.

Figure 10B:
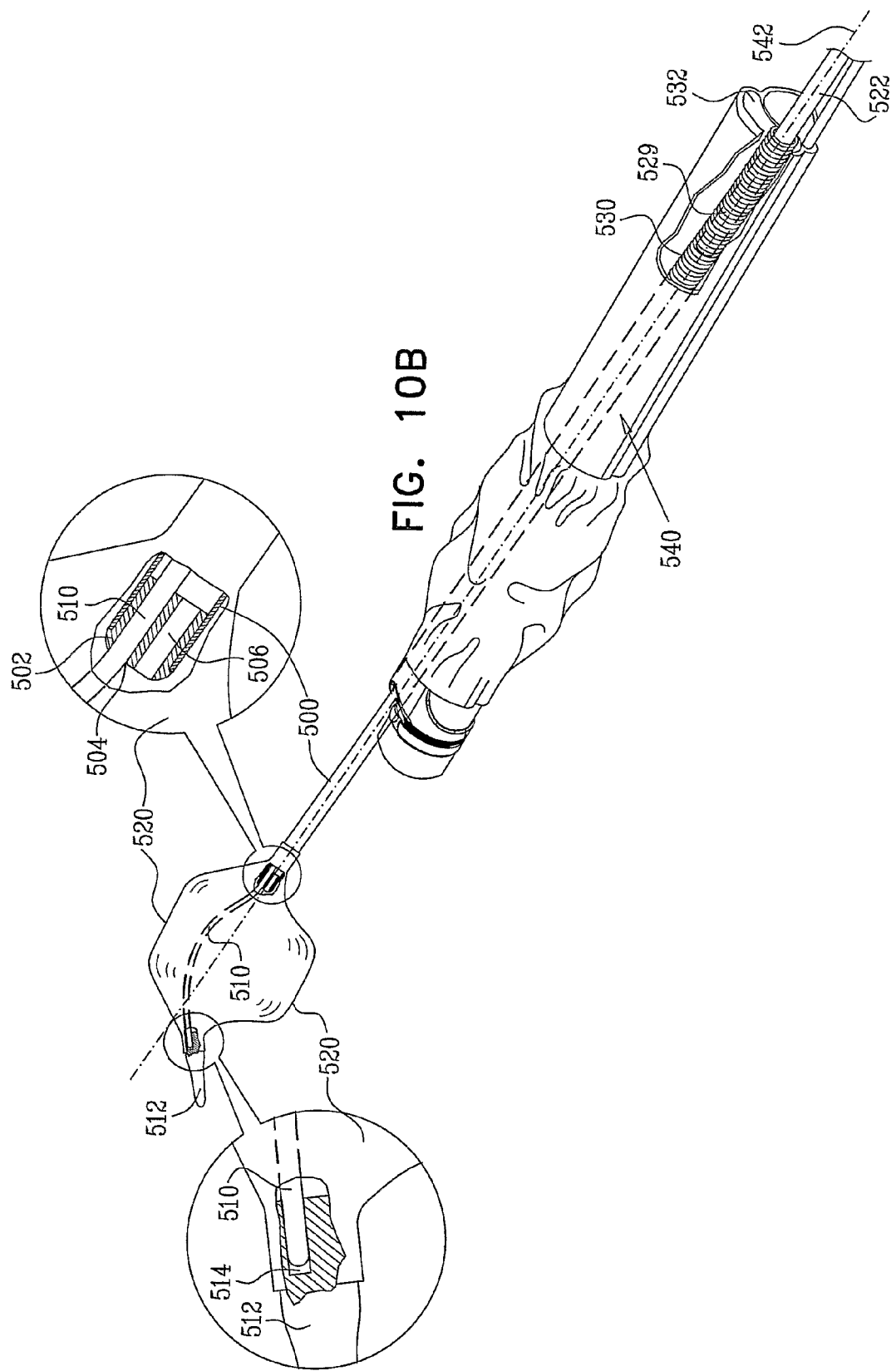

Reference is now made to FIGS. 10A and 10B, which are simplified, partially cut away, partially sectional, illustrations of a balloon catheter/external tube assembly constructed and operative in accordance with a preferred embodiment of the present invention.

As seen in FIGS. 10A & 10B, the balloon catheter/external tube assembly of the present invention preferably comprises an inflation tube 500 which terminates at a cap 502, which is attached at the interior of a distal end of inflation tube 500 and preferably includes at least two lumens, here designated by reference numerals 504 and 506. A guide wire 510 preferably extends through lumen 504 and is fixed to cap 502 thereat, while lumen 506 is open for balloon inflation and deflation.

A distal end of the guide wire 510 preferably is fixed to a tip element 512, preferably within a recess 514 formed therein. A balloon 520 is sealingly fixed, at a proximal end thereof, onto a distal end of inflation tube 500 and, at a distal end thereof, onto a proximal end of tip 512.

The inflation tube 500, guide wire 510 and balloon 520 are at least partially located within an external tube 522. External tube 522, which may be similar in all relevant respects to external tube 122, described hereinabove, may be attached to an endoscope (not shown), such as endoscope 104 (FIGS. 1A & 1B), at multiple locations along its length by any suitable conventional means, such as medical adhesive tape or flexible bands (not shown).

A proximal end 524 of external tube 522 is typically open to enable a proximal end of inflation tube 500 coupled to balloon 520 to extend therefrom outside of a patient's body, thereby enabling insertion, removal and manipulation of the balloon catheter by an operator. Additionally, any other suitable endoscope tool may be inserted, removed or manipulated through tube 522. The proximal end of inflation tube 500 may be coupled to an inflation control assembly, such as inflation control assembly 115 (FIGS. 1A & 1B).

A distal end 529 of external tube 522 preferably extends slidably and telescopically through part of the length of a coil spring 530 which movably and slidably resides within a lumen 532, which preferably forms part of a tubular sleeve 540, which may be similar in all relevant respects to tubular sleeve 110 (FIGS. 1A & 1B). The inflation tube 500, guide wire 510 and balloon 520 are at least partially located within spring 530. Preferably distal end 529 is beveled for ease of passage into and through coil spring 530. It is a particular feature of the present invention that spring 530 defines a generally non-collapsible and highly flexible channel for the balloon catheter.

FIG. 10A shows balloon 520 in a non-inflated, ambient state interior of spring 530 wherein the walls of the balloon 520 are nearly taut but not appreciably tensioned. In this orientation, the guide wire 510 and tip 512 extend along an axis parallel to and spaced from longitudinal axis 542 of the inflation tube 500 and cap 502. FIG. 10B shows balloon 520 in a fully-inflated state forward of the external tube 522 and of spring 530, typically at a pressure of approximately 20-100 millibars. It is seen that inflation of balloon 520 causes guide wire 510 to be bowed in a predetermined direction with respect to axis 542, and to an extent which is a predetermined function of the amount of inflation, thus resulting in a somewhat asymmetric, off-axis, inflated balloon configuration as seen.

According to a preferred embodiment of the present invention, the length of balloon 520 in its non-inflated, ambient state (FIG. 10A) is approximately 40-100 millimeters, and the length of balloon 520 in its fully-inflated state (FIG. 10B) is approximately 30-80 millimeters. In a specific configuration balloon 520, in its non-inflated, ambient state, has a length of 80-95 millimeters, the corresponding length of balloon 520 in its fully-inflated state is 60-75 millimeters, and the diameter of balloon 520 in its fully-inflated state is 30-45 millimeters.

It is appreciated that the angle between the longitudinal axis of tip element 512 and axis 542 in the fully-inflated state (FIG. 10B) may be typically greater than 30 degrees, and may be approximately 90 degrees or more in the specific configuration of balloon 520 described hereinabove. According to a preferred embodiment of the present invention, the angle between the longitudinal axis of the tip element 512 and axis 542 in the fully-inflated state is in the range of 40-75 degrees. Alternatively, the angle between the longitudinal axis of the tip element 512 and axis 542 in the fully-inflated state is in the range of 75-110 degrees.

It is appreciated that torque may be applied to tube 500 and/or guide wire 510, thereby allowing an operator to rotate balloon 520 with tip element 512 around axis 542 during in vivo inspection of a tubular body portion, such as described in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

It is appreciated that inflation pressure in the range of 45-100 millibars may be suitable for anchoring the inflated balloon 520 and thus the balloon catheter to an generally tubular body portion to be inspected or treated, such as the intestine, as described for example in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

It is appreciated that a generally higher inflation pressure may be applied to balloon 520, as suitable. It is appreciated that guide wire 510 is sufficiently flexible to allow its bending during inflation of balloon 520 and to allow balloon 520 to be fully inflated when appropriate inflation pressure is applied.

As seen in FIGS. 10A and 10B, inflation tube 500 protrudes into the internal volume of balloon 520 to a certain extent. In a preferred embodiment of the present invention, tube 500 protrudes between 7 to 20 millimeters into the internal volume of balloon 520. It is appreciated that protrusion of inflation tube 500 into the internal volume of balloon 520 is useful for preventing or reducing blockage of inflation lumen 506 by balloon 520 in case of twisting of balloon 520 around axis 542 while being inflated.

Reference is now made to FIGS. 11A, 11B, 11C, 11D, 11E and 11F, which are simplified, partially cut away, partially sectional, illustrations of the operation of the apparatus of FIGS. 10A & 10B.

Figure 11A:
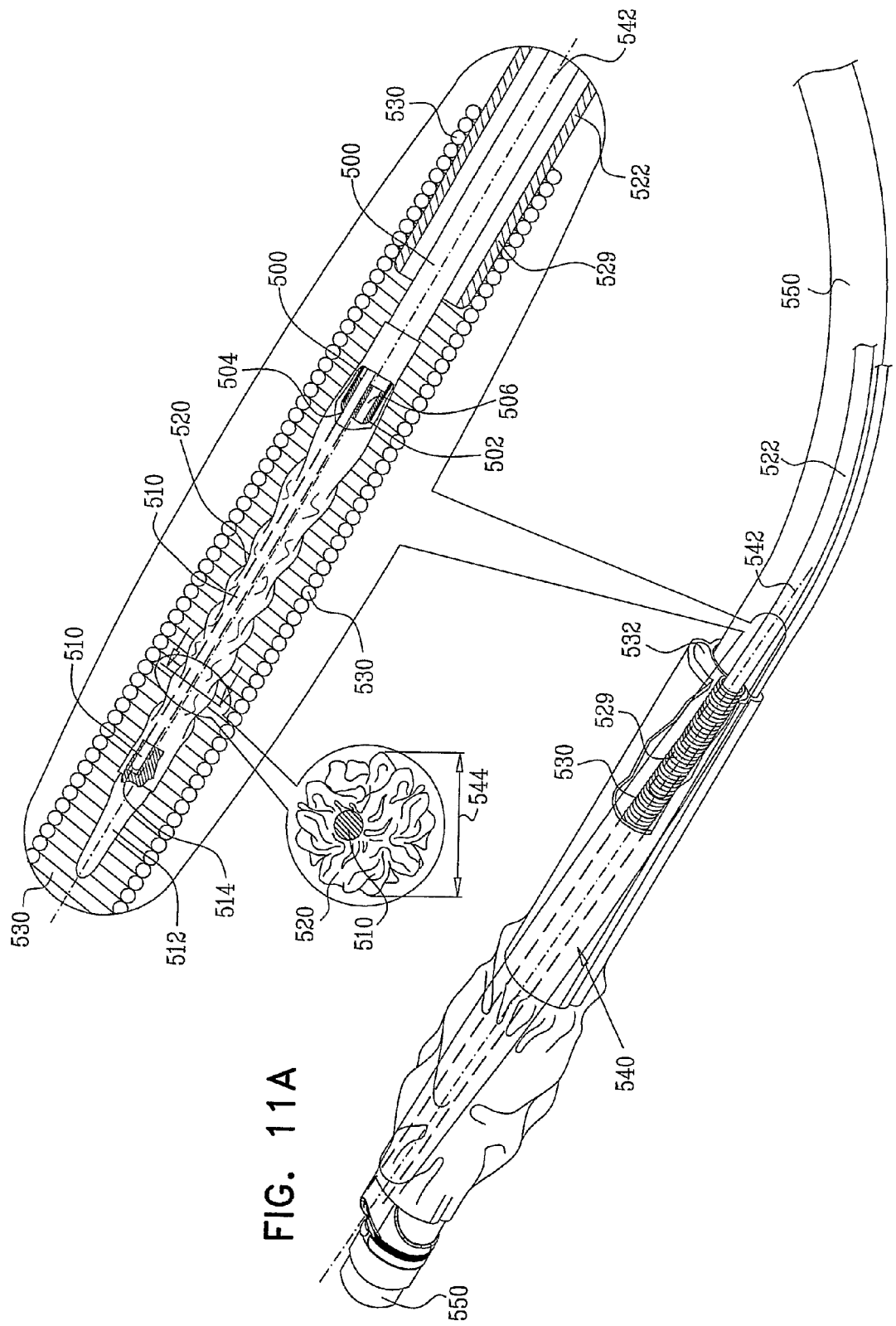
FIGS. 11A, 11B, 11C, 11D, 11E & 11F are simplified, partially cut away, partially sectional, illustrations of the operation of the apparatus of FIGS. 10A and 10B.

FIG. 11A illustrates the application of a partial vacuum, typically about −100 millibars, to the interior of balloon 520 via inflation tube 500 and lumen 506 of cap 502. It is appreciated that due to the nearly taut, but not appreciably tensioned, arrangement of the balloon 520, as described hereinabove with reference to FIG. 10A, the maximum cross-sectional diameter of the balloon catheter, as indicated at reference numeral 544, is relatively small, such as in the range of 2-4 millimeters, and preferably less than 3 mm, and is thus suitable for passage through the external tube 522 when coupled to a conventional endoscope 550.

Figure 11B:
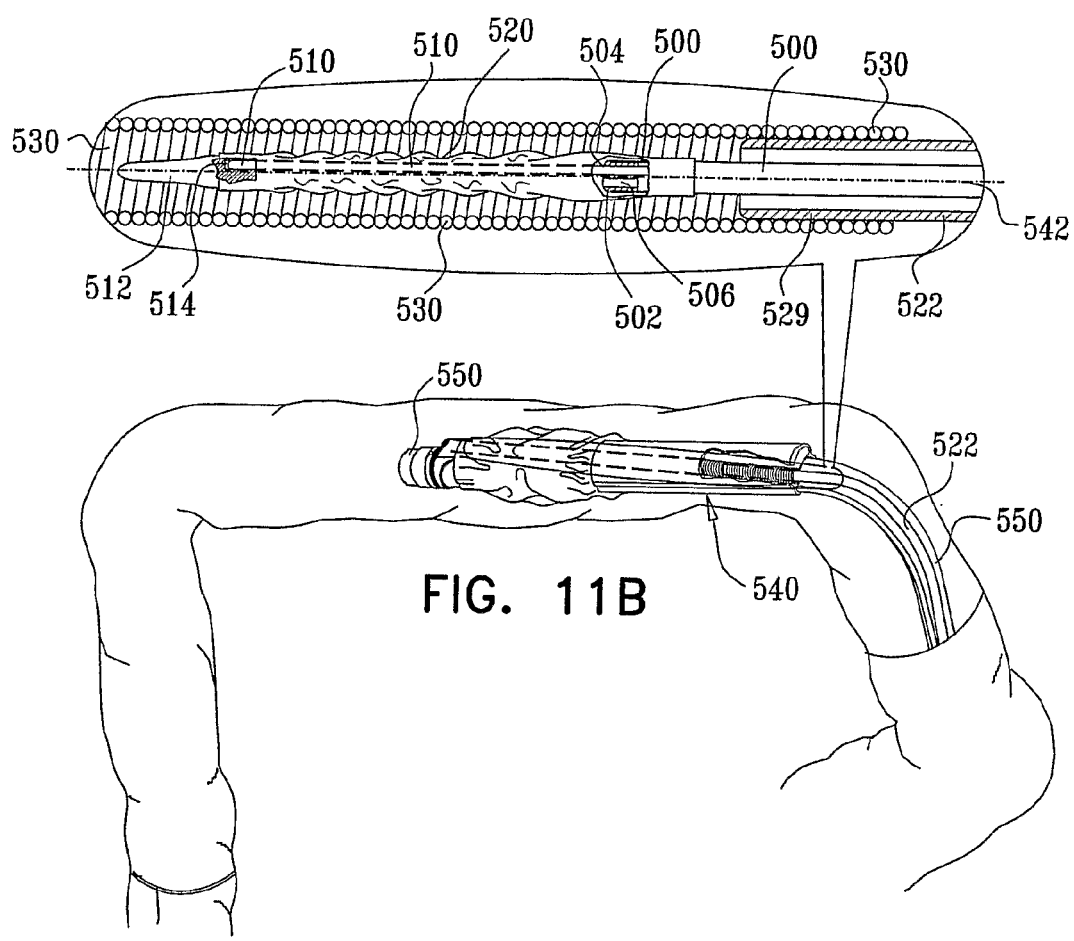

FIG. 11B illustrates the balloon catheter of FIGS. 10A-11A located inside spring 530 interiorly of tubular sleeve 540, forward of external tube 522, located within the intestines of a patient.

Figure 11C:
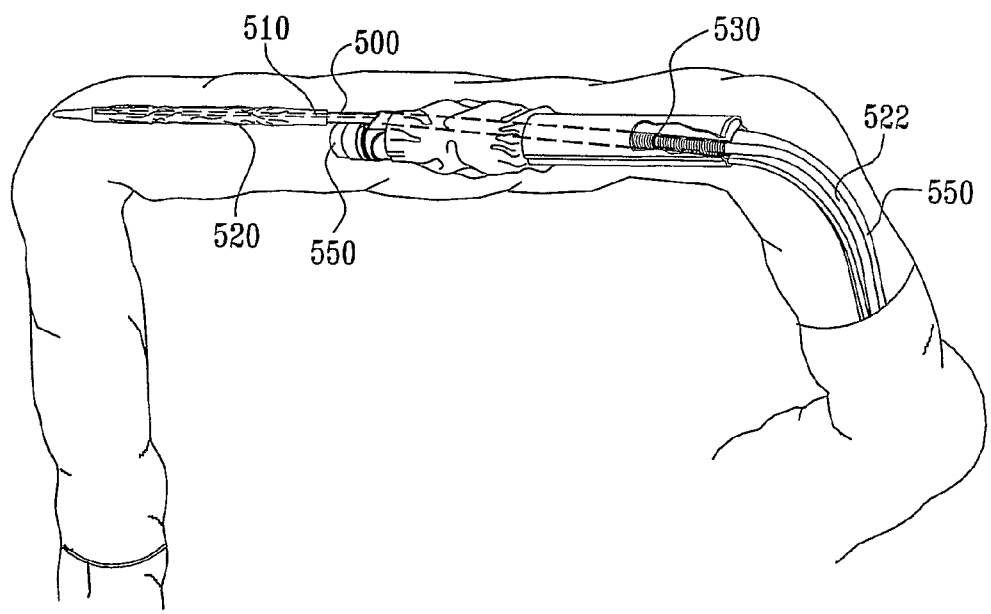
Figure 11D:
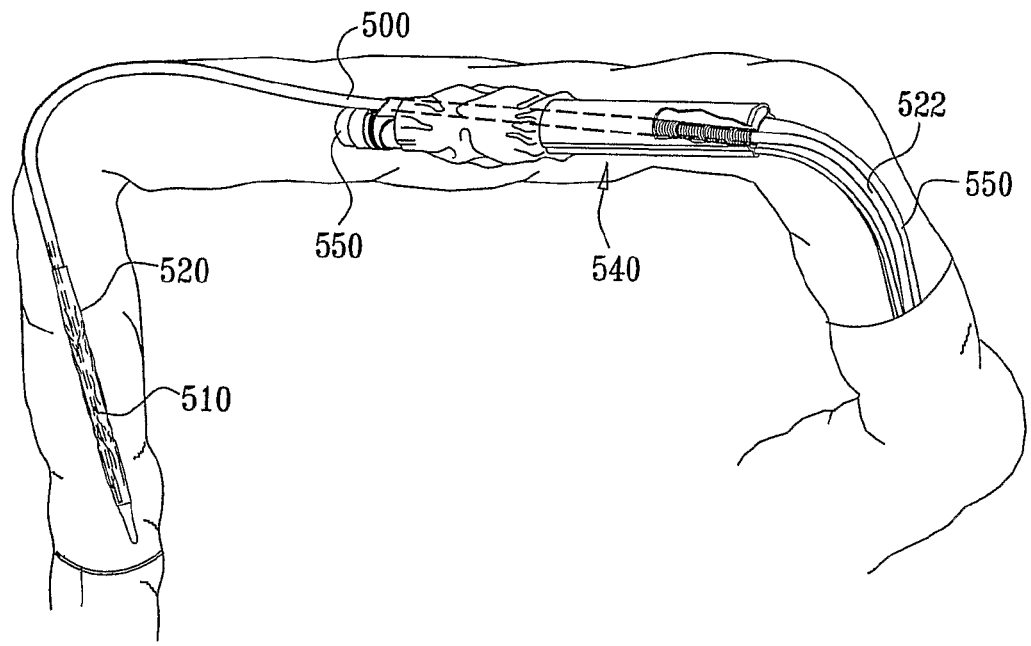
Figure 11E:
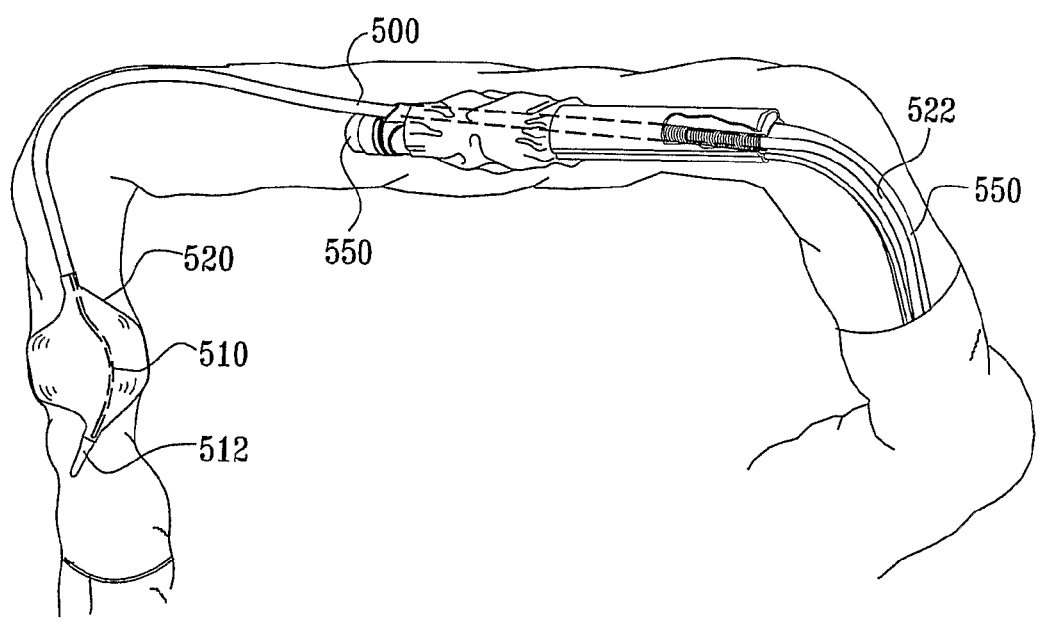

FIG. 11C illustrates the balloon catheter of FIGS. 10A-11B emerging from spring 530. FIG. 11D illustrates the balloon catheter of FIGS. 10A-11C located at an anchoring location forward of the end of the tubular sleeve 540. FIG. 11E illustrates the balloon catheter of FIGS. 10A-11D fully inflated at the anchoring location. It is seen that the guide wire 510 is bowed and thus the balloon 520 is generally asymmetric due to the inflation, as described above.

Figure 11F:
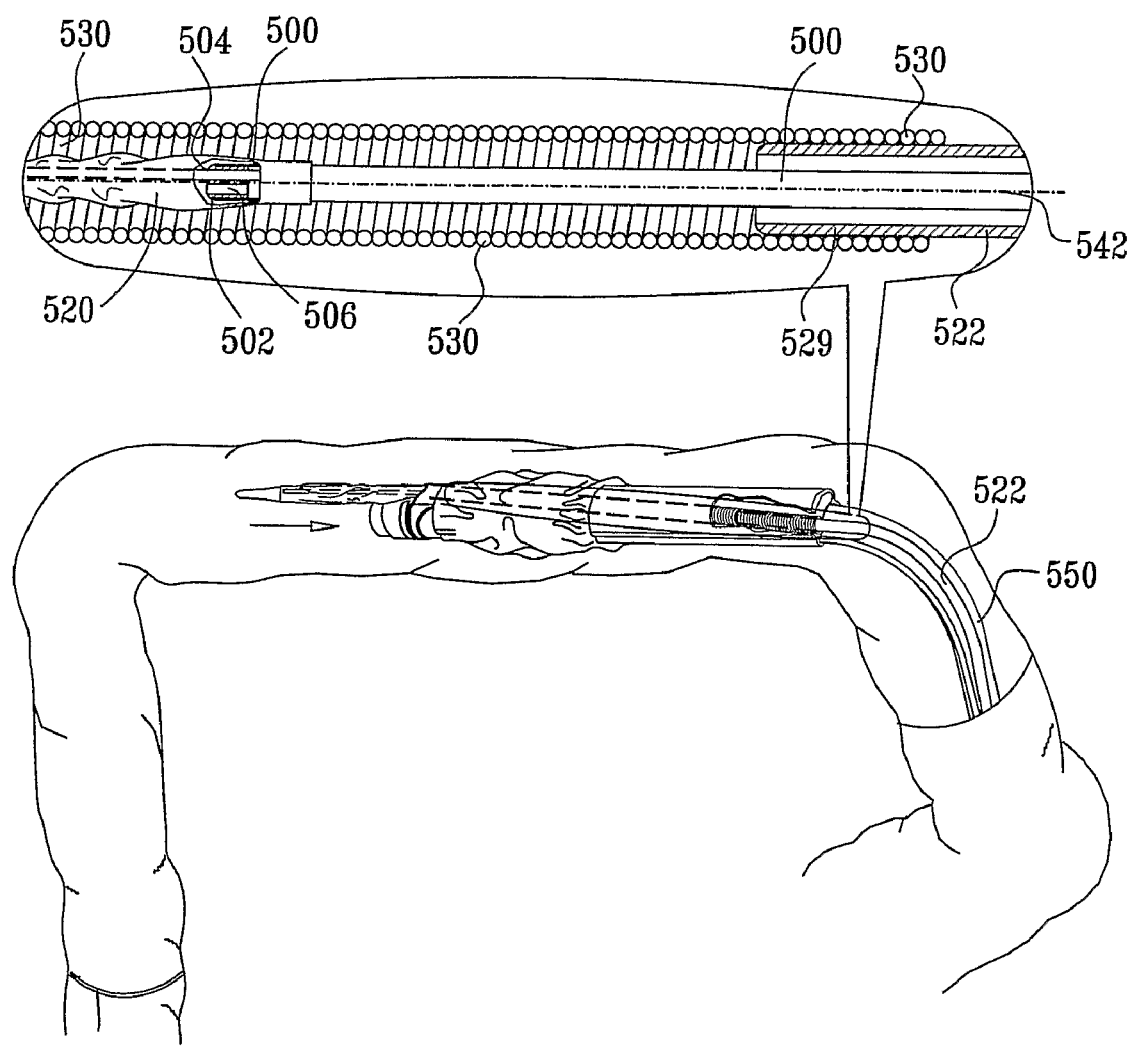

FIG. 11F illustrates deflation of the balloon 520 by application of a partial vacuum, typically about −100 millibars, to the interior of balloon 520 via inflation tube 500 and lumen 506 of cap 502 and reinsertion thereof into spring 530, for removal from the patient or as needed during a procedure, for example for allowing better optical viewing of an organ during endoscopy.

Figure 12:
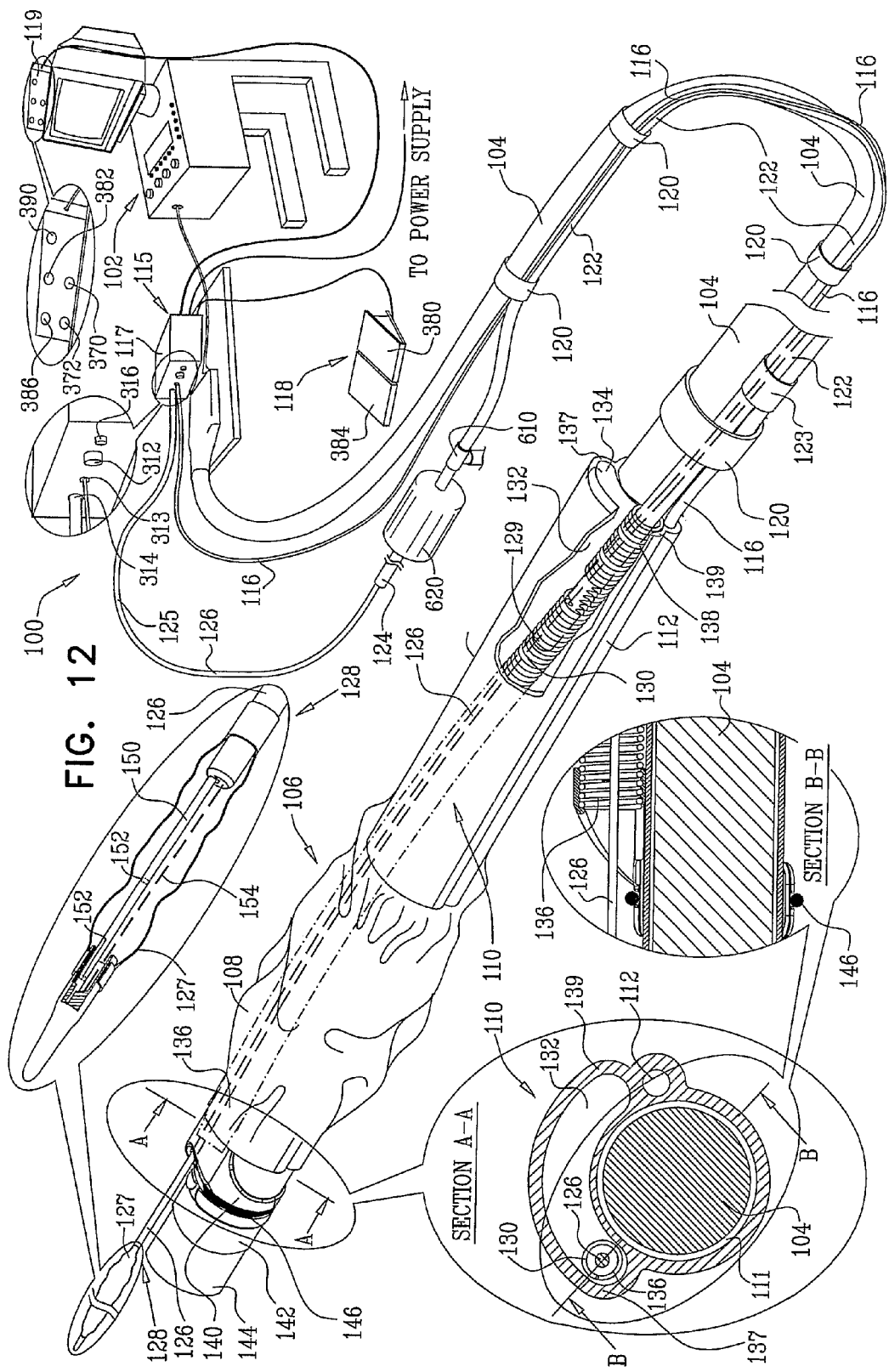
FIG. 12 is a simplified illustration of a flexible endoscope system similar to that shown in FIGS. 1A and 1B.

Reference is now made to FIG. 12, which is a simplified illustration of a flexible endoscope system similar to that shown in FIGS. 1A and 1B. The embodiment of FIG. 12 is identical to that described hereinabove with reference to FIGS. 1A and 1B with the addition of a fluid communication port 610, preferably a 3-port connector in which two of the three ports are arranged in line with the external tube 122, for providing fluid communication with the interior of external tube 122. The embodiment of FIG. 12 also includes a drainage vessel 620, associated with external tube 122 for receiving liquid, such as body fluids, from the interior of external tube 122.

Figure 13A:
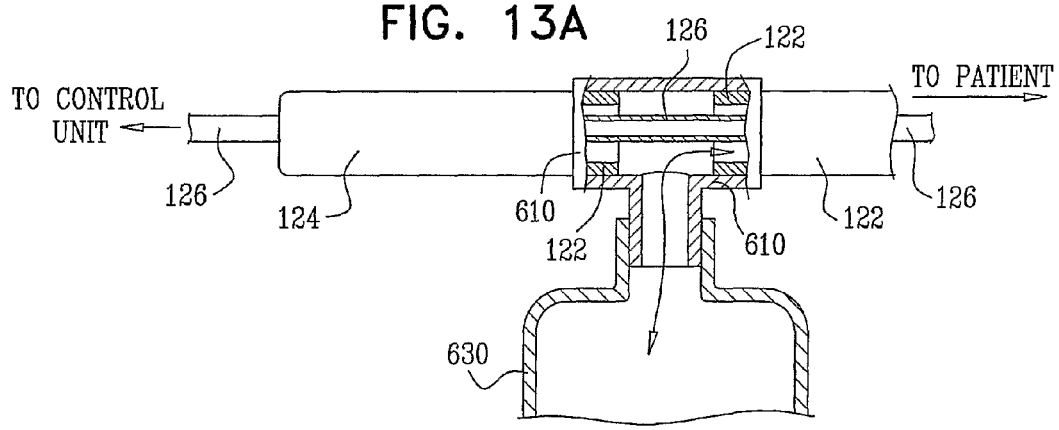
FIGS. 13A and 13B are simplified partially cut away illustrations of portions of the system of FIG. 12.

FIG. 13A illustrates fluid communication port 610 arranged in line with external tube 122 and coupled to a fluid container, line or reservoir 630, which may be, for example, a syringe, a source of gas under positive pressure, a vacuum source or a drainage vessel.

In accordance with a preferred embodiment of the present invention, an outer surface of inflation tube 126, shown interiorly of external tube 122 and of port 610, may be coated with a hydrophilic coating. A commercially available, hydrophilic coated, inflation tube 126 is a Slipskin™ coated PVC tube, available from MCTec of 9 Edisonstraat, Venlo, Netherlands. If water or a water-soluble material is injected into the external tube 122 outside of inflation tube 126, passage of inflation tube 126 through external tube 122 is greatly facilitated by a resulting reduction in friction.

Figure 13B:
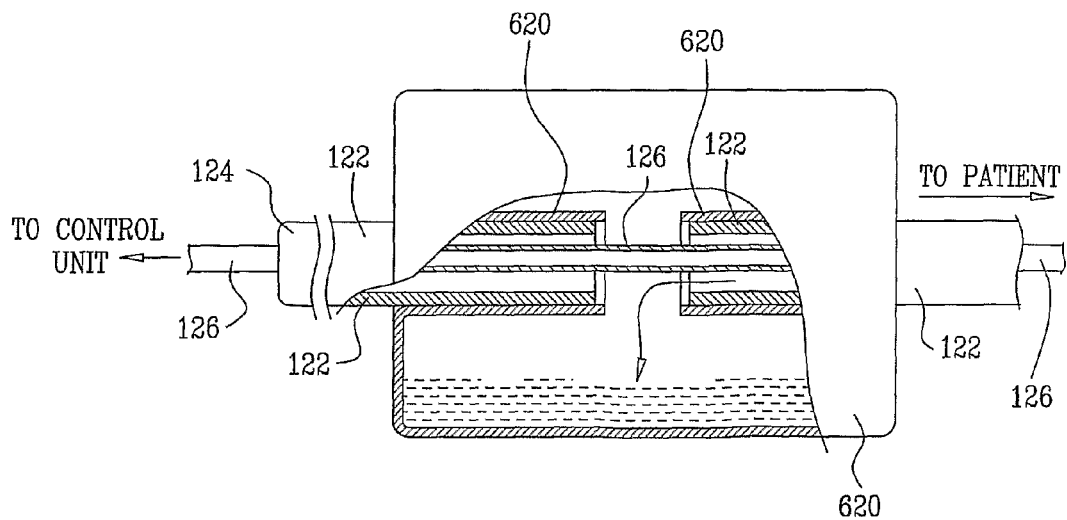

FIG. 13B illustrates drainage vessel 620 coupled in-line with external tube 122 and configured as a cylinder which is coaxial with external tube 122 to allow collection of drainage liquid irrespective of the orientation of the external tube 122.

Reference is now made to FIGS. 14A, 14B, 14C & 14D, which are simplified, partially cut away, partially sectional, illustrations of the operation of an endoscope tool 128 as shown and described hereinabove with reference to FIGS. 2A-3B, including a balloon catheter 399 as shown and described hereinabove with reference to FIGS. 8A & 8B, extending through an instrument channel 440 of an endoscope 442, such as that shown and described hereinabove with reference to FIGS. 9B-9F, in a specific context, the junction between the colon and the small intestine at the ileo-cecal valve, designated by reference numeral 650.

Figure 14A:
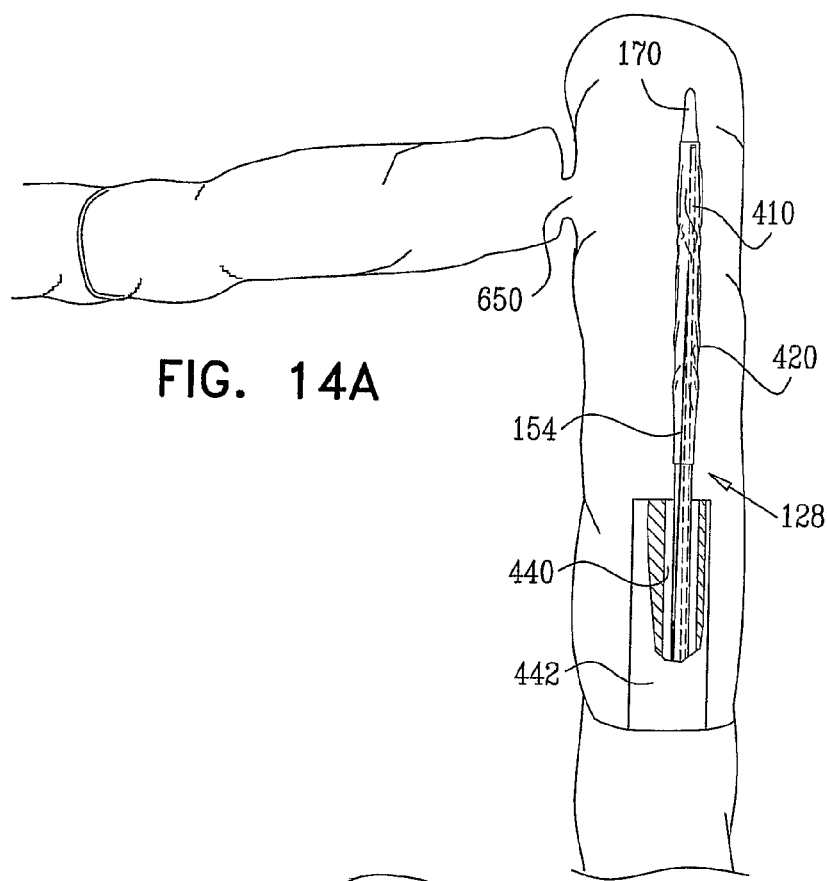
FIGS. 14A, 14B, 14C & 14D are simplified, partially cut away, partially sectional, illustrations of the operation of an endoscope tool as shown and described hereinabove with reference to FIGS. 2A-3B, including a balloon catheter as shown and described hereinabove with reference to FIGS. 8A & 8B, together with an endoscope, such as that shown and described hereinabove with reference to FIGS. 9B-9F.
Figure 14B:
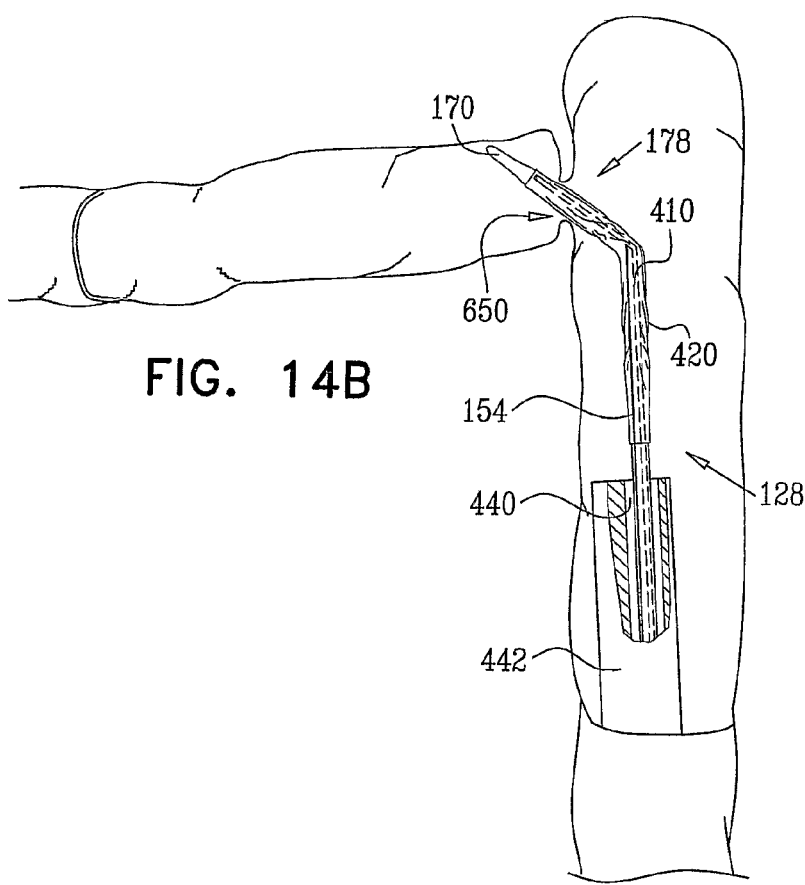
Figure 14C:
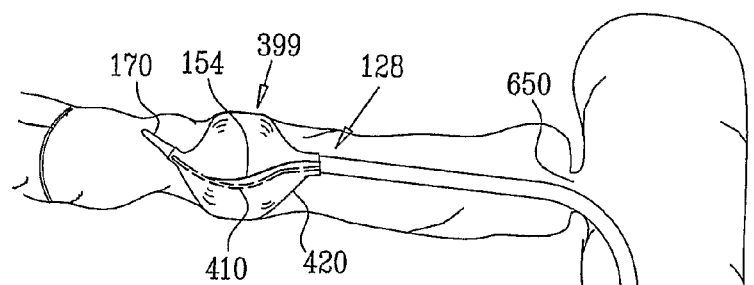
Figure 14D:
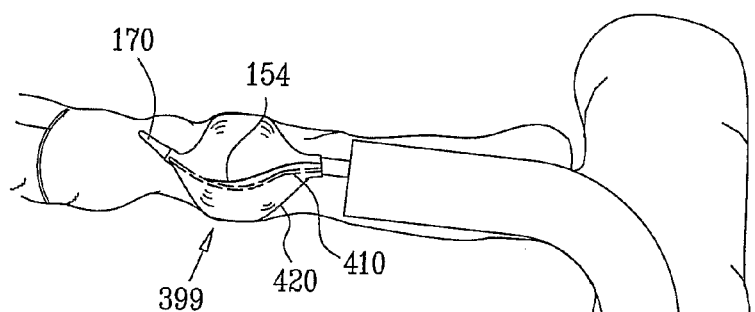

FIGS. 14A and 14B together show bending of endoscope tool 128, located in the colon, such that distal portion 178 and tip element 170 are directed through ileo-cecal valve 650. FIG. 14C shows anchoring of the balloon catheter 399 in the small intestine by inflation of balloon 420, causing bowing of guide wire 410. FIG. 14D shows forward displacement of endoscope 442 along endoscope tool 128 through the ileo-cecal valve 650.

Figure 15A:
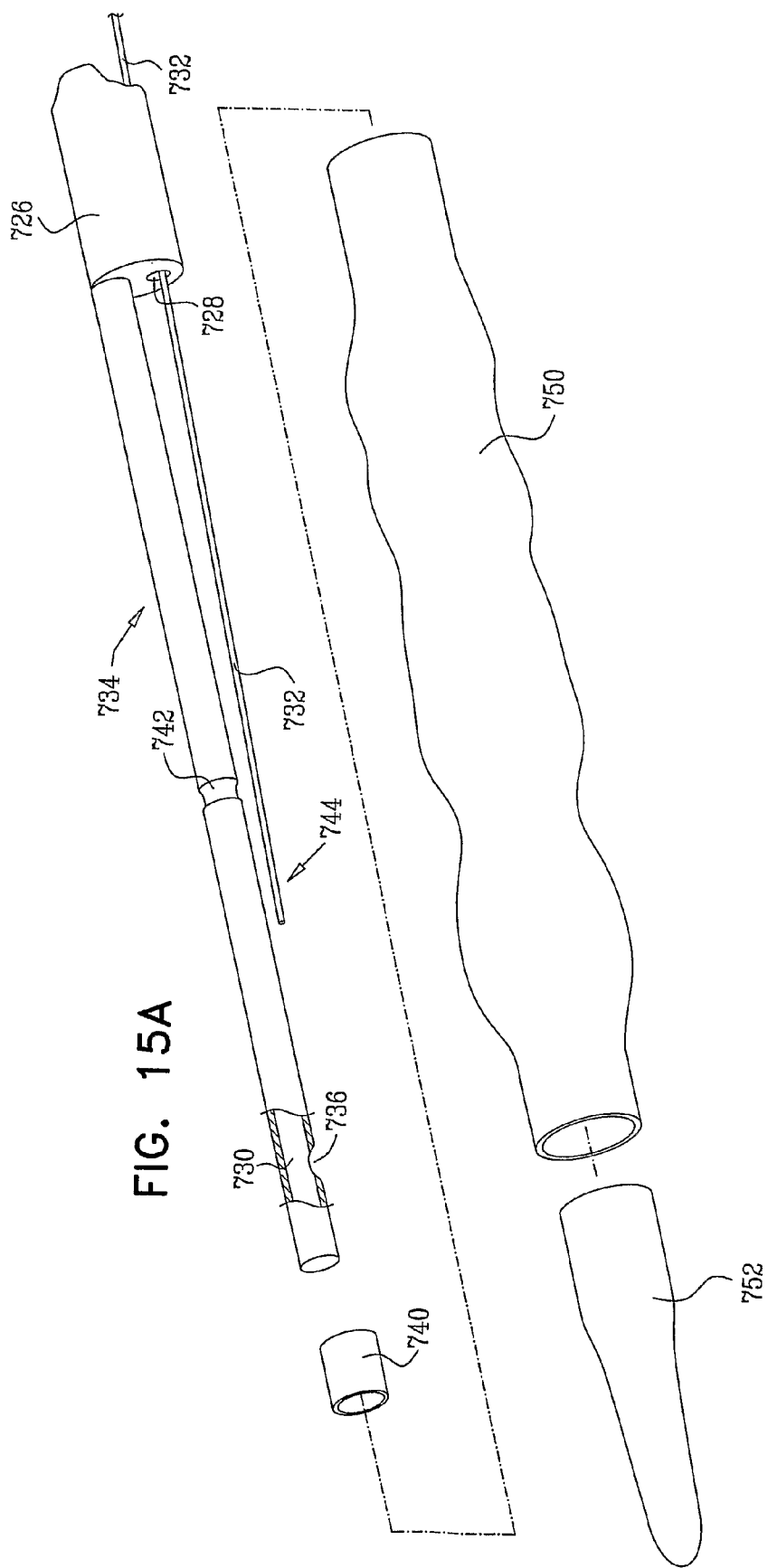
FIGS. 15A and 15B are respective exploded and partially cut-away pictorial illustrations of a catheter or endoscope tool and associated inflation tube, constructed and operative in accordance with another preferred embodiment of the present invention.
Figure 15B:
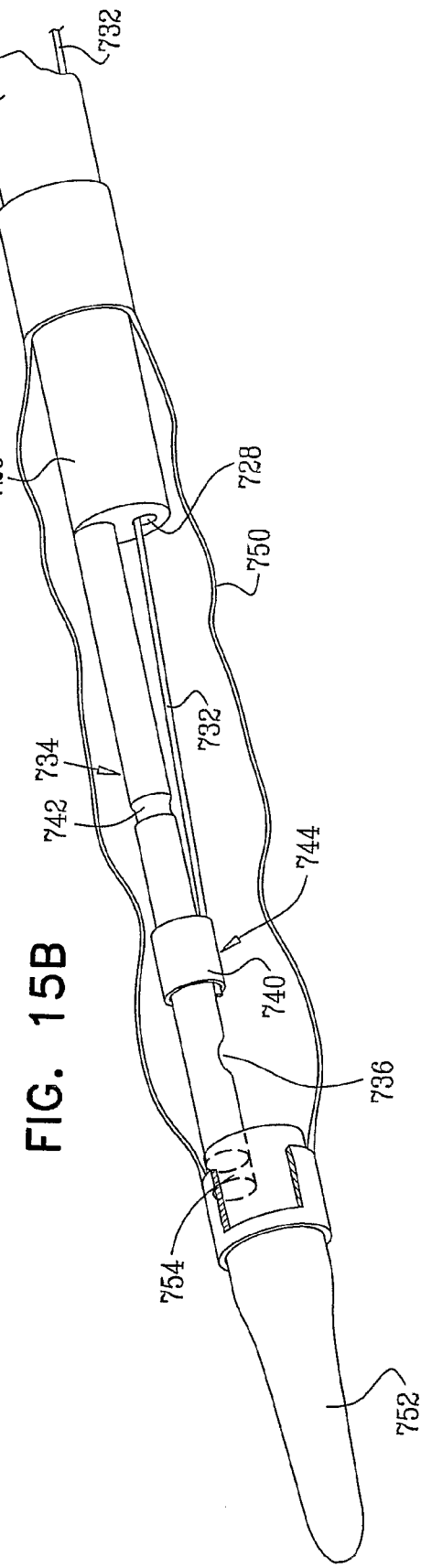

Reference is now made to FIGS. 15A and 15B, which are respective exploded and partially cut-away pictorial illustrations of a catheter or endoscope tool and associated inflation tube, constructed and operative in accordance with another preferred embodiment of the present invention.

As seen in FIGS. 15A & 15B, an inflation tube 726 preferably includes at least two lumens, here designated by reference numerals 728 and 730. A selectable steering wire 732 preferably extends through lumen 728. Lumen 730 is a balloon inflation lumen and extends through a relatively narrow distal portion 734 of the inflation tube which extends forward of distal end of lumen 728 and communicates with a balloon inflation port 736.

A collar 740 preferably fixedly attaches a distal end of selectable steering wire 732 to the distal portion 734 forwardly of at least one indentation 742. In this embodiment, the attachment location, designated by reference numeral 744, of the distal end of the selectable steering wire 732 to the distal portion 734 of the inflation tube 726 by collar 740 lies within a balloon 750.

A distal end of the distal portion 734 of the inflation tube 726 preferably is fixed to a tip element 752, preferably within a recess 754 formed therein. Balloon 750 is sealingly fixed, at a proximal end thereof, onto a distal end of inflation tube 726 and, at a distal end thereof, onto a proximal end of tip element 752.

Reference is now made to FIGS. 16A & 16B, which are sectional illustrations of the catheter or endoscope tool of FIGS. 15A & 15B in respective straight and bent operative steering orientations. FIG. 16A shows the catheter or endoscope tool extending along a longitudinal axis 760. In FIG. 16B, it is seen that when selectable steering wire 732 is retracted relative to inflation tube 726, as indicated by arrow 762, it applies a pulling force to a forward part of the distal portion 734 lying forwardly of at least one indentation 742, causing that forward part of distal portion 734 and tip element 752 to rotate in a direction indicated by arrow 770 relative to longitudinal axis 760. Preferably the distal portion 734 is sufficiently resilient under such bending so as to return to its axial orientation shown in FIG. 16A once selectable steering wire 732 is released.

It is appreciated that torque may be applied to inflation tube 726, thereby allowing an operator to rotate balloon 750 with tip element 752 around axis 760 during in vivo inspection of a tubular body portion, such as described in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

Figure 17A:
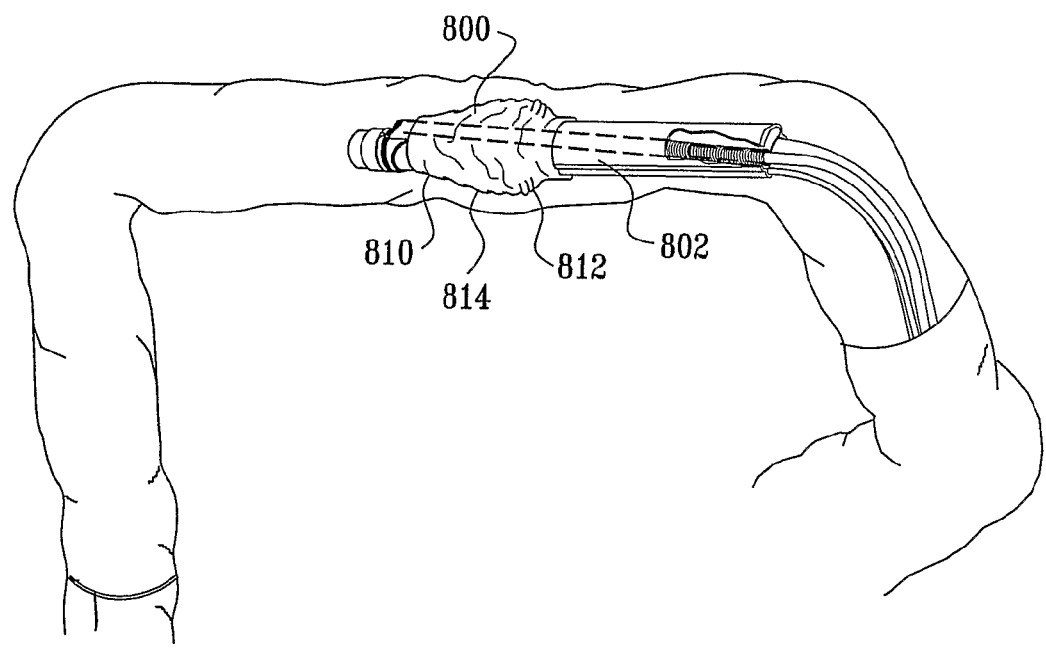
FIGS. 17A and 17B are simplified illustrations of a portion of an alternative embodiment of the flexible endoscope system of FIGS. 1A and 1B.
Figure 17B:
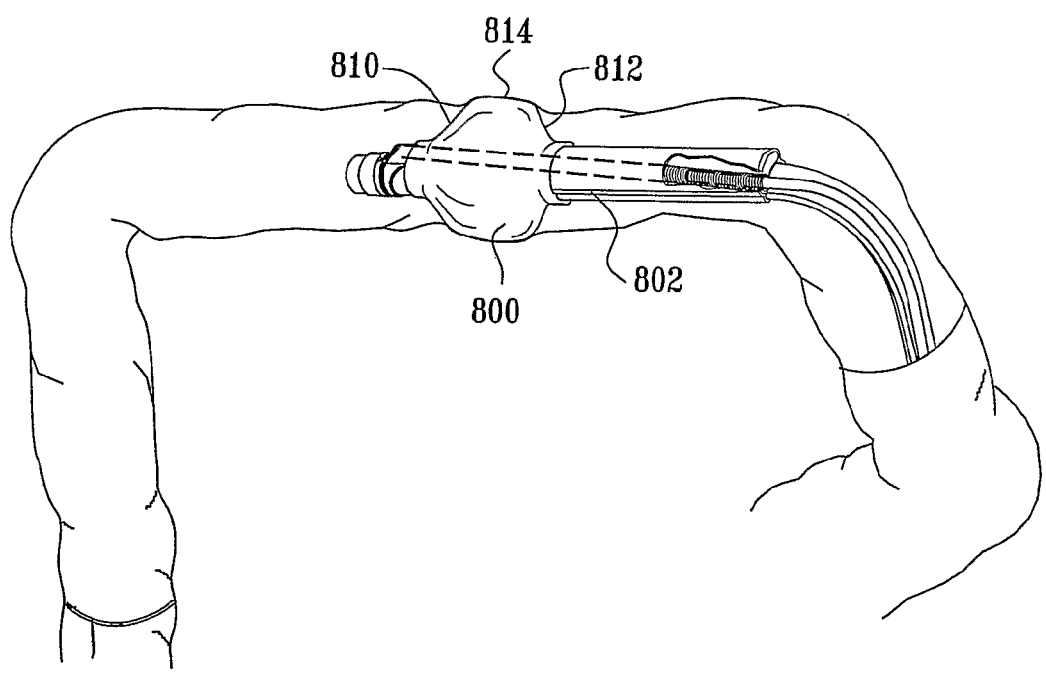

Reference is now made to FIGS. 17A and 17B, which are simplified illustrations of a portion of an alternative embodiment of the flexible endoscope system of FIGS. 1A and 1B, in respective deflated and inflated operative orientation at an anchoring location in the small intestine. As seen, a peripheral balloon 800 surrounds a tubular sleeve 802, which may be similar in all relevant respects to tubular sleeve 110 (FIGS. 1A & 1B).

Preferably, peripheral balloon 800 includes a forward facing portion 810 and a rearward facing portion 812, separated by a central portion 814. It is a particular feature of the present invention that both the forward facing portion 810 and the rearward facing portion 812 are tapered, both when deflated, as seen in FIG. 17A, and when inflated, as seen in FIG. 17B. It is a further particular feature of the present invention that the slope of the forward facing portion 810 is different than, greater than and opposite to that of rearward facing portion 812.

According to a preferred embodiment of the present invention, the slope of rearward facing portion 812, when inflated, is greater than 45 degrees and more preferably greater than 60 degrees, and the slope of the forward facing portion 810, when inflated, is less than 60 degrees and more preferably less than 45 degrees.

In a specific embodiment of the present invention, the slope of the forward facing portion 810 is approximately 45 degrees and the slope of the rearward facing portion 812 is approximately 60 degrees. This is particularly helpful during an endoscopy procedure, as described for example in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

For example, a small slope of forward facing portion 810 when the balloon 800 is not fully inflated may allow more efficient and lower friction advancement of an endoscope assembly for in vivo inspection of a generally tubular body portion such as an intestine, as described for example in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

A high slope of rearward facing portion 812, for example, may prevent or minimize slippage and undesired withdrawal of an endoscope assembly during in vivo inspection of a generally tubular body portion such as an intestine, as described for example in one or more of applicant/assignee's PCT Application No. PCT/IL2005/000152, filed Feb. 7, 2005; PCT Application No. PCT/IL2005/000849, filed Aug. 8, 2005, and PCT Application No. PCT/IL2007/000600, filed May 17, 2007, the disclosures of which are hereby incorporated by reference.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specifications and which are not in the prior art.

The invention claimed is:

1. A catheter comprising:

a tube having at least one lumen;

at least one elongate element, at least part of which is extendable forwardly of a distal end of said tube to a fixed orientation at which a distal end of said at least one elongate element extends beyond said distal end of said tube by a fixed amount; and at least one selectably inflatable balloon communicating with at least one of said at least one lumen, said at least one selectably inflatable balloon having a forward end and a rearward end, said rearward end of said balloon being located adjacent said distal end of said tube at a rearward balloon end mounting location and said forward end of said balloon being located adjacent a distal end of said at least one elongate element at a forward balloon end mounting location, wherein said balloon is configured such that when said at least one elongate element is in said fixed orientation and said balloon is in a deflated operative orientation, the distance between said rearward balloon end mounting location and said forward balloon end mounting location is greater than the distance between said rearward balloon end mounting location and said forward balloon end mounting location when said balloon is in an inflated operative orientation, said balloon being symmetric and said at least one elongate element being incompressible along its length, whereby inflation of said balloon causes bending of said at least one elongate element and said bending of said at least one elongate element causes said balloon to assume an asymmetric inflated balloon configuration.

2. A catheter according to claim 1 and wherein the distance between said rearward balloon end mounting location and said forward balloon end mounting location is greater than the distance between said rearward balloon end mounting location and said forward balloon end mounting location when said balloon is in an inflated operative orientation by at least 20%.

3. A catheter according to claim 1 and wherein said bending of said at least one elongate element is in a predetermined direction.

4. A catheter according to claim 1 and wherein inflation of said at least one selectably inflatable balloon causes said distal end of said at least one elongate element to rotate relative to a longitudinal axis of said catheter by at least 40 degrees.

* * * * *